US012773127B2

(12) United States Patent
Kobayashi et al.

(10) Patent No.: US 12,773,127 B2
(45) Date of Patent: Oct. 27, 2026

(54) MOTION STATE MONITORING SYSTEM, MOTION STATE MONITORING METHOD, AND NON-TRANSITORY COMPUTER READABLE MEDIUM STORING MOTION STATE MONITORING PROGRAM

(71) Applicant: TOYOTA JIDOSHA KABUSHIKI KAISHA, Toyota (JP)

(72) Inventors: Makoto Kobayashi, Nisshin (JP); Taiga Matsumoto, Nagoya (JP); Takeru Fukagawa, Kariya (JP); Shuhao Chang, Kitanagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 207 days.

(21) Appl. No.: 18/822,714

(22) Filed: Sep. 3, 2024

(65) Prior Publication Data

US 2025/0127424 A1 Apr. 24, 2025

(30) Foreign Application Priority Data

Oct. 24, 2023 (JP) ................................. 2023-182857

(51) Int. Cl.
*A61B 5/11* (2006.01)
*A61B 5/00* (2006.01)

(52) U.S. Cl.
CPC ........... *A61B 5/1114* (2013.01); *A61B 5/1121* (2013.01); *A61B 5/684* (2013.01); *A61B 5/742* (2013.01); *A61B 5/1124* (2013.01)

(58) Field of Classification Search
CPC .................. A61B 5/1114; A61B 5/684; A61B 2562/0219; A61B 5/1118; A61B 5/6802
See application file for complete search history.

(56) References Cited

U.S. PATENT DOCUMENTS

| | | | | |
|---|---|---|---|---|
| 9,271,532 | B2 * | 3/2016 | Cole | A41D 1/089 |
| 2016/0192856 | A1 * | 7/2016 | Lee | A61B 5/0006 600/382 |
| 2016/0262687 | A1 * | 9/2016 | Vaidyanathan | A61B 5/0205 |
| 2017/0209096 | A1 | 7/2017 | Ishii et al. | |

(Continued)

FOREIGN PATENT DOCUMENTS

| | | |
|---|---|---|
| JP | 2014-208257 A | 11/2014 |
| JP | 2017-128837 A | 7/2017 |

(Continued)

*Primary Examiner* — Christian Jang
(74) *Attorney, Agent, or Firm* — Oliff PLC

(57) ABSTRACT

A motion state monitoring system according to the present disclosure is configured to monitor a motion state at a target part of the body of a subject, and includes: a measuring instrument configured to measure a motion state; and a motion state monitoring apparatus configured to monitor the motion state, in which the measuring instrument includes: a sensor configured to detect the motion state; and a holding part configured to hold the sensor, the holding part includes a bag formed of a stretchable member, the bag includes an insertion opening extending in one direction and being configured to hold the sensor inserted through the insertion opening thereinside, and when the holding part holding the sensor thereinside is attached to the target part, the holding part is attached to the target part in such a manner that the bag stretches in the one direction.

12 Claims, 13 Drawing Sheets

(56) References Cited

U.S. PATENT DOCUMENTS

| | | | | |
|---|---|---|---|---|
| 2022/0054042 | A1 | 2/2022 | Kobayashi et al. | |
| 2022/0054044 | A1 | 2/2022 | Kobayashi et al. | |
| 2022/0054045 | A1 | 2/2022 | Kobayashi et al. | |
| 2022/0057233 | A1 | 2/2022 | Kobayashi et al. | |
| 2022/0117500 | A1* | 4/2022 | Wiese .................. | A61B 5/6804 |
| 2023/0050179 | A1 | 2/2023 | Ishii et al. | |

FOREIGN PATENT DOCUMENTS

| | | | |
|---|---|---|---|
| JP | 2018-503414 | A | 2/2018 |
| JP | 2022-034407 | A | 3/2022 |
| JP | 2022-034448 | A | 3/2022 |
| JP | 2022-034449 | A | 3/2022 |
| JP | 2022-034450 | A | 3/2022 |
| JP | 2023-020895 | A | 2/2023 |
| WO | 2016/081776 | A1 | 5/2016 |

* cited by examiner

| Attaching Position | Target Part | Initial Reference Direction (Angle $\theta_0$ [° ] from $Z_S$-axis) |
|---|---|---|
| 20-1 | Right Upper Arm | 5 |
| 20-2 | Right Forearm | 10 |
| 20-3 | Head | 0 |
| 20-4 | Chest | 0 |
| 20-5 | Waist | 0 |
| 20-6 | Left Upper Arm | -5 |
| 20-7 | Left Forearm | -10 |
| 20-8 | Right Thigh | 0 |
| 20-9 | Right Lower Leg | 0 |
| 20-10 | Left Thigh | 0 |
| 20-11 | Left Lower Leg | 0 |

Fig. 9

| Attaching Angle $\theta_1$ | Rotation Angle Calculation Order |
|---|---|
| 0° | X-axis → Z-axis → Y-axis |
| 90° | Y-axis → Z-axis → X-axis |

Fig. 14

MOTION STATE MONITORING SYSTEM, MOTION STATE MONITORING METHOD, AND NON-TRANSITORY COMPUTER READABLE MEDIUM STORING MOTION STATE MONITORING PROGRAM

CROSS REFERENCE TO RELATED APPLICATIONS

This application is based upon and claims the benefit of priority from Japanese patent application No. 2023-182857, filed on Oct. 24, 2023, the disclosure of which is incorporated herein in its entirety by reference.

BACKGROUND

The present disclosure relates to a motion state monitoring system, a motion state monitoring method, and a motion state monitoring program.

Japanese Unexamined Patent Application Publication No. 2022-034450 discloses a motion state monitoring system that monitors a motion state at a target part of a subject's body. The motion state monitoring system disclosed in Japanese Unexamined Patent Application Publication No. 2022-034450 includes a sensor attached to a target part, and an attaching pad and a belt-like band as a mechanism for attaching the sensor. The sensor is connected to the band attached to the target part with the attaching pad interposed therebetween.

SUMMARY

When an arm or the like of a subject is paralyzed, a therapist needs to attach the sensor to the body (e.g., the arm) of the subject by moving the subject's arm. When doing so, winding the band around the arm or the like while adjusting the orientation of the sensor is difficult and time-consuming. Further, the sensor may drop from the attaching pad.

The present disclosure has been made in order to solve the above-described problem, and an object thereof is to provide a motion state monitoring system, a motion state monitoring method, and a motion state monitoring program capable of reducing the time taken to attach a sensor and preventing the sensor from being dropped.

A motion state monitoring system according to an aspect of the present disclosure is a motion state monitoring system configured to monitor a motion state at a target part of a subject's body, including: a measuring instrument configured to measure the motion state; and a motion state monitoring apparatus configured to monitor the motion state, in which the measuring instrument includes: a sensor configured to detect the motion state; and a holding part configured to hold the sensor, the holding part includes a bag formed of a stretchable member, the bag includes an insertion opening extending in one direction and is configured to hold thereinside the sensor inserted through the insertion opening, and when the holding part holding thereinside the sensor is attached to the target part, the holding part is attached to the target part in such a manner that the bag stretches in the one direction.

In the above-described motion state monitoring system, the bag may include a cloth as a material, and a lid configured to cover the insertion opening.

In the above-described motion state monitoring system, the measuring instrument may further include an attaching part configured to be attached to the target part, and the holding part may be attached to the target part with the attaching part stretchable in the one direction interposed therebetween.

In the above-described motion state monitoring system, a hole may be formed at a part corresponding to a predetermined position in the target part in each of the holding part and the attaching part, and a part of the attaching part located on a side thereof on which the subject's body is located may be black.

In the above-described motion state monitoring system, the holding part may be attached to the attaching part by hook-and-loop fasteners.

In the above-described motion state monitoring system, the holding part may include a transparent part configured to let light emitted from a light emitting unit provided in the sensor pass therethrough.

In the above-described motion state monitoring system, the motion state monitoring apparatus includes: an acquisition unit configured to acquire sensing information of the sensor attached to the target part; an attaching direction detecting unit configured to detect an attaching direction of the sensor; and a control processing unit configured to output sensing-related information related to the sensing information in association with the attaching direction of the sensor.

In the above-described motion state monitoring system, the attaching direction of the sensor may be an attaching direction with respect to a direction determined in advance according to the target part.

In the above-described motion state monitoring system, the attaching direction of the sensor may be an attaching direction with respect to an axial direction of the attaching part attached to the target part.

In the above-described motion state monitoring system, the control processing unit may output, in response to detection of an event in which the attaching direction changes during measurement by the sensor, the sensing-related information obtained after the event in association with the changed attaching direction after the event.

In the above-described motion state monitoring system, the control processing unit may perform an arithmetic processing according to the attaching direction on the sensing information or the sensing-related information, and output a result of the arithmetic processing in association with the attaching direction of the sensor. The control processing unit may output the sensing-related information by using an algorithm obtained by performing machine learning using the attaching direction and the sensing-related information as learning data.

A motion state monitoring method according to an aspect of the present disclosure is a motion state monitoring method for monitoring a motion state at a target part of a subject's body by using a motion state monitoring system, in which the motion state monitoring system includes: a measuring instrument configured to measure the motion state; and a motion state monitoring apparatus configured to monitor the motion state, the measuring instrument includes: a sensor configured to detect the motion state; and a holding part configured to hold the sensor, the holding part includes a bag formed of a stretchable member, the bag includes an insertion opening extending in one direction and is configured to hold thereinside the sensor inserted through the insertion opening, when the holding part holding thereinside the sensor is attached to the target part, the holding part is attached to the target part in such a manner that the bag stretches in the one direction, and the motion state monitoring method includes: acquiring sensing information of a sensor attached to the target part; detecting an attaching direction of the sensor; and outputting sensing-related information related to the sensing information in association with the attaching direction of the sensor.

A motion state monitoring program according to an aspect of the present disclosure is a motion state monitoring program for causing a computer included in a motion state monitoring system to monitor a motion state at a target part of a subject's body, in which the motion state monitoring system includes: a measuring instrument configured to measure the motion state; and a motion state monitoring apparatus configured to monitor the motion state, the measuring instrument includes: a sensor configured to detect the motion state; and a holding part configured to hold the sensor, the holding part includes a bag formed of a stretchable member, the bag includes an insertion opening extending in one direction and is configured to hold thereinside the sensor inserted through the insertion opening, when the holding part holding thereinside the sensor is attached to the target part, the holding part is attached to the target part in such a manner that the bag stretches in the one direction, and the motion state monitoring program is configured to cause the computer to perform: acquiring sensing information of a sensor attached to the target part; detecting an attaching direction of the sensor; and outputting sensing-related information related to the sensing information in association with the attaching direction of the sensor.

According to the present disclosure, it is possible to provide a motion state monitoring system, a motion state monitoring method, and a motion state monitoring program capable of reducing the time taken to attach a sensor and preventing the sensor from being dropped.

The above and other objects, features and advantages of the present disclosure will become more fully understood from the detailed description given hereinbelow and the accompanying drawings.

BRIEF DESCRIPTION OF DRAWINGS

FIG. 9 is a table for explaining the initial reference direction in the motion state monitoring system according to the first embodiment;

FIG. 14 shows an example of a data structure of an arithmetic processing table used by a control processing unit in a motion state monitoring system according to a second embodiment;

DESCRIPTION OF EMBODIMENTS

A specific configuration according to an embodiment will be described hereinafter with reference to the drawings. The following description is for showing preferred embodiments according to the present disclosure, and the scope of the present disclosure is not limited to the below-shown embodiments. Further, not all the components/structures described in the embodiments are necessarily indispensable as means for solving the problem. For clarifying the description, the following description and drawings are partially omitted and simplified as appropriate. Further, the same symbols are assigned to the same or corresponding components throughout the drawings, and redundant descriptions thereof are omitted as appropriate.

First Embodiment

Figure 1:
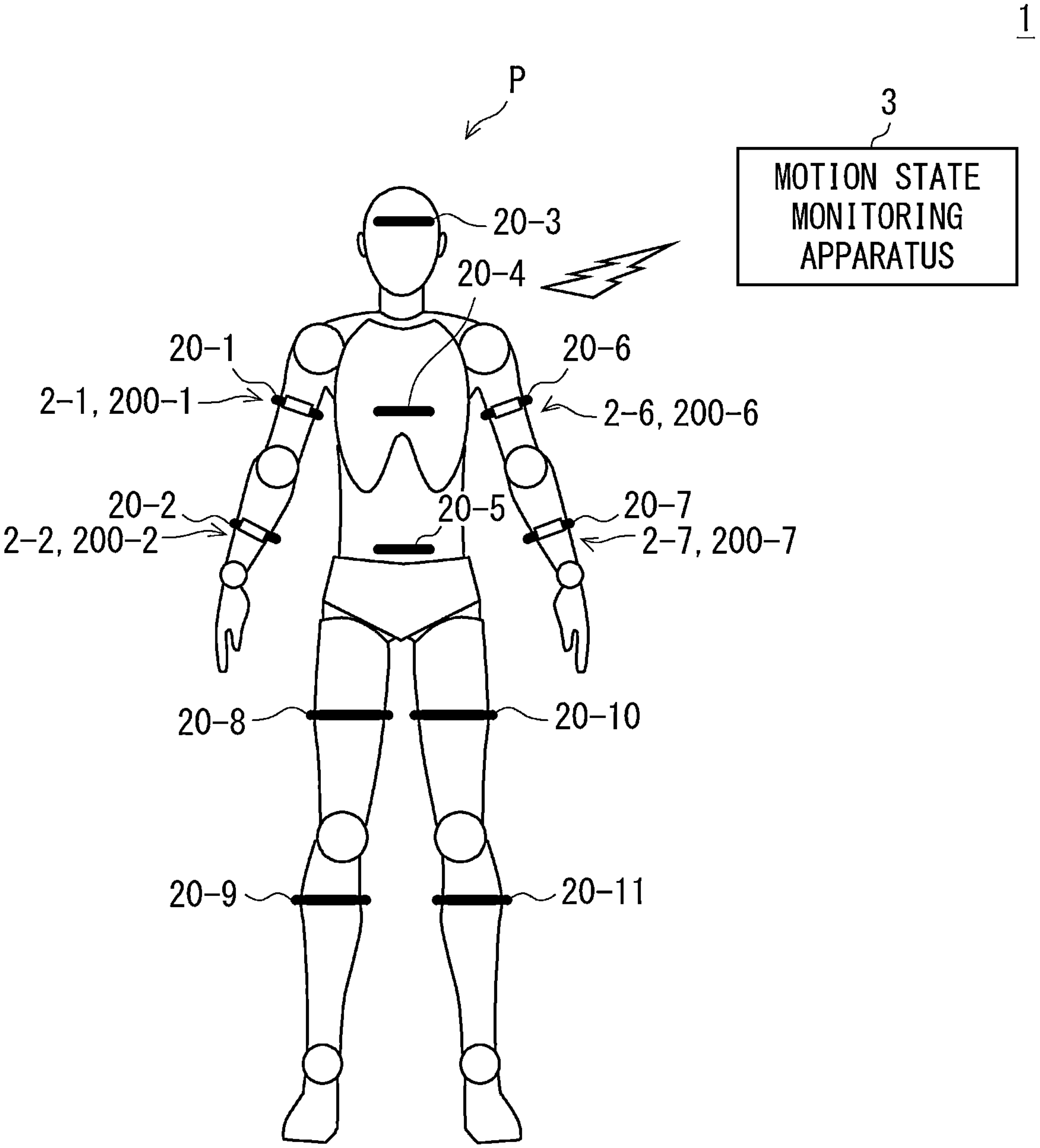
FIG. 1 is a structural diagram showing an example of a motion state monitoring system according to a first embodiment.

Firstly, a motion state monitoring system according to a first embodiment will be described. FIG. 1 is a configuration diagram showing an example of a motion state monitoring system 1 according to the first embodiment. The motion state monitoring system 1 monitors a motion state of a part of the body of a subject P. Further, the motion state monitoring system 1 supports the motion performed by the subject P based on the monitoring result of the motion of the subject P so that the motion of the subject P gets closer to a desired motion. Specifically, the motion state monitoring system 1 measures the motion function of the subject P, who is, for example, a rehabilitation trainee or an elderly person. Then, the motion state monitoring system 1 supports the training performed by the subject P by analyzing, evaluating, and managing the results of the measurement. The subject P performs a motion test with sensors 200 attached to predetermined parts of his/her body. For example, the motion test is a motion function test for measuring the motion state at a part of the body of the subject P when the subject P performs a designated motion, and thereby measuring his/her motion function. Examples of the motion state monitoring system 1 includes a training support system.

Hereinafter, the designated motion is referred to as a monitoring target motion. The monitoring target motion is determined corresponding to the part of the body. Examples of the monitoring target motion include flexion and extension of shoulder, adduction and abduction of shoulder, lateral and medial rotations of shoulder, flexion and extension of neck, medial rotation of neck, flexion and extension of elbow, lateral and medial rotation of hip, pronation and external rotation of forearm, and thoracolumbar lateral flexion. Note that when the target part is either left or right body part, the monitoring target motion may be separately determined for the left or right body part. A part to be monitored is referred to as a target part. As the target part, one or a plurality of parts may be associated with one monitoring target motion, and the same part may be associated with different monitoring target motions.

As shown in FIG. 1, the motion state monitoring system 1 includes measuring instruments 2 and a motion state monitoring apparatus 3. The motion state monitoring apparatus 3 may be referred to as the motion state monitoring system 1. The motion state monitoring apparatus 3 is an apparatus that monitors motion states at target parts of the body of the subject P. Note that measuring instruments 2-1, 2-2, . . . , and the like shown in the drawing are collectively referred to as the measuring instruments 2.

The measuring instruments 2 measure the motion states at the target parts of the body of the subject P. Specifically, the measuring instrument 2 (i.e., each measuring instrument 2) a measuring apparatus that measures the moving direction and the moving amount of the target part. The measuring instrument 2 (i.e., each measuring instrument 2) includes a sensor 200 for detecting a motion state. In this embodiment, the measuring instrument 2 may include an acceleration sensor and an angular velocity sensor. The measuring instrument 2 measures the acceleration and angular velocity of the measuring instrument 2 itself. Specifically, the measuring instrument 2 may include a three-axis acceleration sensor and a three-axis angular velocity sensor. In this case, the measuring instrument 2 measures moving amounts in the three-axis directions, i.e., the XYZ-axis directions, and rotation angles around the three axes. Note that the measurement axes are not limited to three axes, and instead may be two or fewer axes. Further, the measuring instrument 2 may include a geomagnetic sensor for detecting geomagnetism and measuring a direction in which the measuring instrument 2 itself is oriented. Note that sensors 200-1, 200-2, . . . , and the like shown in the drawing are collectively referred to as the sensors 200.

Each of the measuring instruments 2 is connected to the motion state monitoring apparatus 3 so that they can communicate with each other. In this embodiment, communication between each measuring instrument 2 and the motion state monitoring apparatus 3 is short-range wireless communication such as Bluetooth (Registered Trademark), NFC (Near Field Communication) or ZigBee. However, the communication is not limited to these examples, and may be wireless communication through a network such as a wireless LAN (Local Area Network). Further, the communication may be wired communication through the Internet, a LAN, a WAN (Wide Area Network), or a network formed by a combination thereof.

The measuring instrument 2 (i.e., each measuring instrument 2) includes, in addition to the sensor 200, an attaching mechanism for the sensor 200 (e.g., a holding part, an attaching part, and the like). Further, the sensor 200 is attached to an attaching position 20 corresponding to the target part of the body of the subject P through the attaching mechanism. Note that in order to cope with the measurement of various monitoring target parts, each of a plurality of sensors 200 is associated with a respective one of a plurality of target parts of the body of the subject P and can be attached to the associated target part. In the drawing, the target parts at which the sensors 200 can be attached are indicated as attaching positions 20-1, 20-2, . . . , and 20-11. Each of the attaching positions 20-1, 20-2, . . . , and 20-11 is associated with a respective one of the sensors 200-1, 200-2, . . . , and 200-11. For example, attaching positions 20-1, 20-2, . . . , and 20-11 are referred to as the right upper arm, right forearm, head, chest (trunk), waist (pelvis), left upper arm, left forearm, right thigh, right lower leg, left thigh, and left lower leg, respectively. The associations between the attaching positions 20 and the sensors 200 are made by pairing between the sensors 200 and the motion state monitoring apparatus 3 in advance and associating identification information (ID) of the attaching positions 20 with the IDs of the sensors 200 in an application of the motion state monitoring apparatus 3. Note that the attaching positions 20-1, 20-2, . . . , and the like are collectively referred to as the attaching positions 20.

In this embodiment, the attaching positions 20 used in the motion test is selected from the attaching positions 20-1 to 20-11 according to the monitoring target motion selected by a user. Note that the user refers to a user who uses the motion state monitoring apparatus 3 and is, for example, the subject P himself/herself or a staff member who carries out the motion test. Further, the subject P or the staff member attaches the sensors 200 (in this drawing, the sensors 200-1, 200-2, 200-6 and 200-7) associated with the selected attaching positions 20 (in this drawing, attaching positions 20-1, 20-2, 20-6 and 20-7) of the body of the subject P, and then starts the motion test.

Note that although the plurality of sensors 200 associated with the plurality of attaching positions 20, respectively, are prepared in the above example, the number of prepared attaching positions 20 may be one. Further, the number of prepared sensors 200 may be one.

The sensor 200 (e.g., each sensor 200) starts measurement in response to the start of the motion test and transmits sensing information to the motion state monitoring apparatus 3. The sensing information may include acceleration information, angular velocity information, or quaternion information. Further, the sensing information may include a component in each of the measurement axis directions (X, Y and Z-axis directions). Further, the sensor 200 stops the measurement in response to the end of the motion test.

The motion state monitoring apparatus 3 monitors the motion states at the target parts of the body of the subject P during the motion test. Further, the motion state monitoring apparatus 3 analyzes, evaluates, and manages information about the motion states. Examples of the motion state monitoring apparatus 3 include a computer apparatus. Specifically, examples of the motion state monitoring apparatus 3 may include a personal computer, a notebook computer, a mobile phone, a smartphone, a tablet-type terminal, or other communication terminal apparatus capable of receiving/outputting data. Further, examples of the motion state monitoring apparatus 3 may include a server computer. This embodiment is described under the assumption that the motion state monitoring apparatus 3 is a tablet-type terminal.

The motion state monitoring apparatus 3 is used by the user during the motion test, and before and after the motion test. The motion state monitoring apparatus 3 receives the choice of the monitoring target motion from the user, and notifies the user of the attaching positions 20 corresponding to the target parts. Then, the motion state monitoring apparatus 3 transmits a request for starting or stopping the measurement to the sensors 200 in response to the start or end of the motion test.

Further, the motion state monitoring apparatus 3 outputs sensing-related information as the measurement result in response to the reception of the sensing information from the sensors 200. Note that the sensing-related information indicates information related to the sensing information, and may include the sensing information itself. Alternative, the sensing-related information may be information obtained by performing various conversion processes on the sensing information. Further, the sensing-related information may be information obtained by performing arithmetic processing based on the sensing information. The sensing-related information may include information about the above-described motion state. Note that the information related to the above-described motion state may include sensing-related information. That is, the information about the motion states may be information based on the sensing-related information or may include the sensing-related information itself.

The motion state monitoring apparatus 3 may be connected to an external server (not shown) through a network so that they can communicate with each other. The external server may be a computer apparatus or a cloud server on the Internet. In this case, the motion state monitoring apparatus 3 may transmit the sensing-related information or the information about the motion state of the subject P held by the motion state monitoring apparatus 3 itself to the external server.

Figure 2:
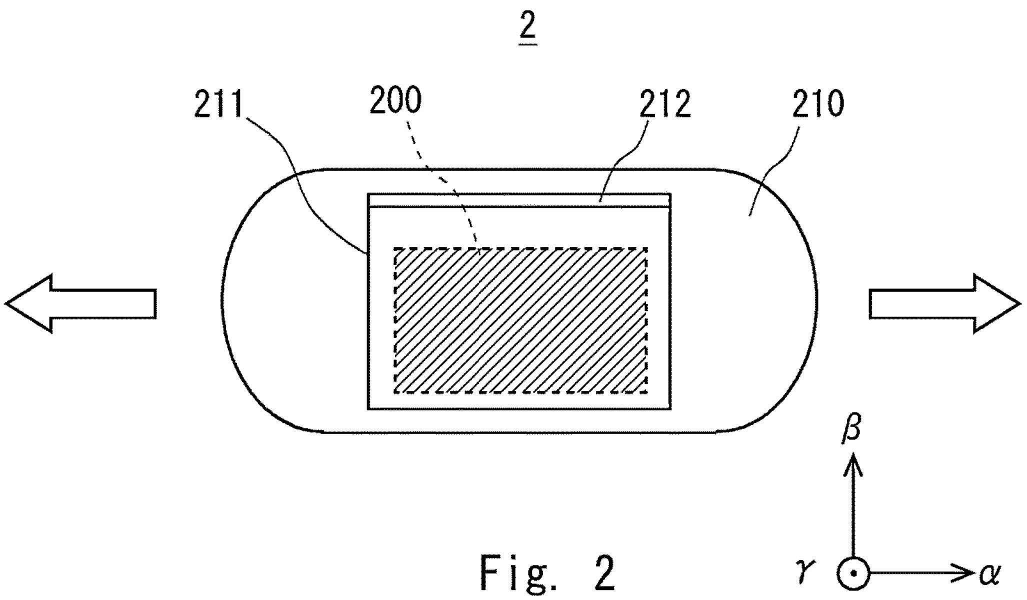
FIG. 2 is an explanatory diagram showing an example of an attaching mechanism of a sensor of a measuring instrument in the motion state monitoring system according to the first embodiment.
Figure 3:
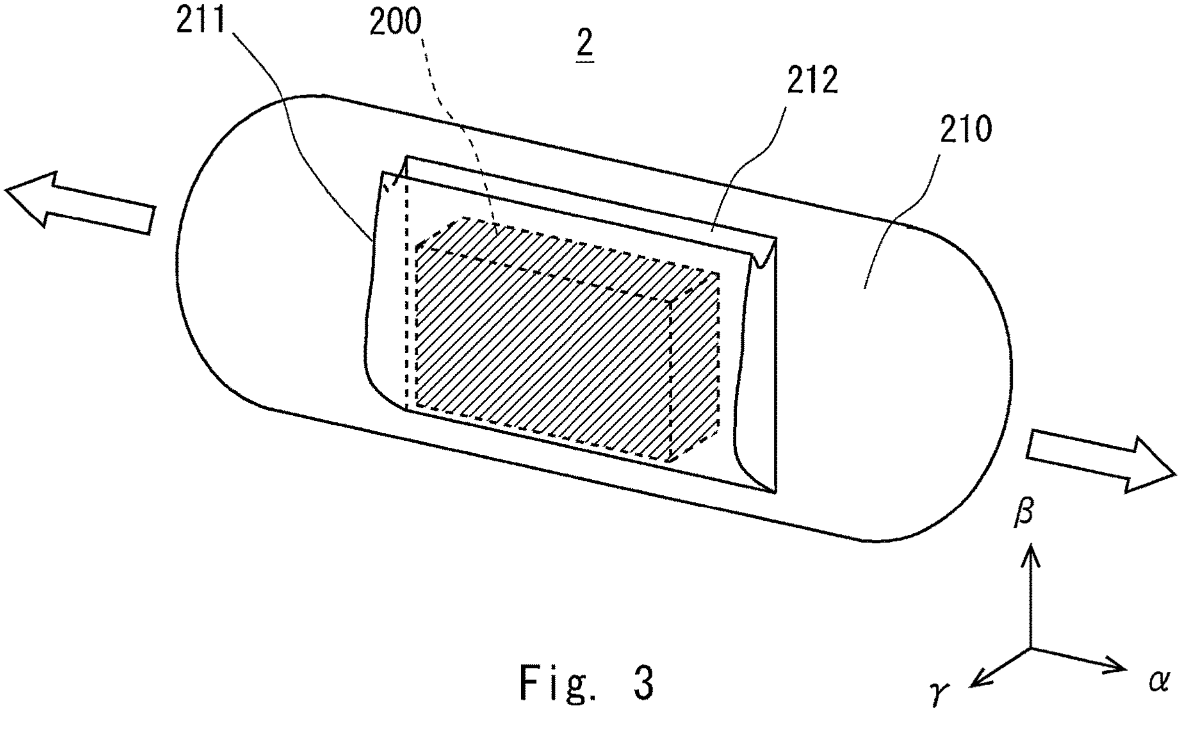
FIG. 3 is an explanatory diagram showing an example of an attaching mechanism of a sensor of a measuring instrument in the motion state monitoring system according to the first embodiment.

A mechanism for attaching a measuring instrument 2 will be described hereinafter with reference to FIGS. 2 to 7. FIGS. 2 to 7 are explanatory diagrams showing an example of an attaching mechanism of the sensor 200 of a measuring instrument 2 in the motion state monitoring system 1 according to the first embodiment. FIG. 3 is a perspective view of what is shown in FIG. 2.

As shown in FIGS. 2 and 3, the measuring instrument 2 includes a holding part 210 as an attaching mechanism (attaching member). Therefore, the measuring instrument 2 includes the sensor 200 and the holding part 210. Note that in order to explain the attaching mechanism of the measuring instrument 2, an αβγ-orthogonal coordinate axis system is introduced. The direction in which the holding part 210 extends is defined as an α-axis direction, and two directions orthogonal to the β-axis are defined as a β-axis direction and a γ-axis direction, respectively. Note that the αβγ-orthogonal coordinate axis system may or may not correspond to the XYZ-orthogonal coordinate axis system which is the measurement coordinate axis system.

The holding part 210 holds the sensor 200. The holding part 210 may be referred to as an attaching pad. The holding part 210 may include a bag 211 formed of a stretchable member. The bag 211 may include a cloth as a material. Note that not only the bag 211 but also the holding part 210 may include a cloth as a material. Further, the stretchable member is not limited to the cloth, and the bag 211 may include a stretchable resin member such as rubber or vinyl as the stretchable member.

The bag 211 includes an insertion opening 212 extending in one direction. The one direction is, for example, the α-direction. The bag 211 holds the sensor 200 inserted through the insertion opening 212 thereinside. The bag 211 has, for example, a rectangular shape with sides extending in the α- and β-axis directions. Note that the shape of the bag 211 is not limited to the rectangular shape, but may be an elliptic shape or the like as long as the sensor 200 can be held thereinside. Further, the bag 211 may include a cut-out such as a hole in a part thereof, or may include a member different from the rest of the bag in a part thereof. The insertion opening 212 is formed on, for example, the edge of the bag 211 on the positive side thereof in the β-axis direction. Further, the sensor 200 is inserted from the insertion opening 212 in the β-axis negative direction. Note that the side of the bag 211 on which the insertion opening 212 is formed is not limited to the edge of the bag 211 on the positive side thereof in the β-axis direction and may be formed in the central part of the bag 211 as long as the insertion opening 212 extends in the one direction.

When the holding part 210 holding the sensor 200 in the bag 211 is attached to the target part of the body of the subject P, the holding part 210 is attached to the target part in such a manner that the bag 211 stretches in the one direction. As the bag 211 starches in the one direction, for example, in the α-axis direction, the insertion opening 212 also stretches in the a-axis direction. In this way, it is possible to prevent the insertion opening 212 from being opened in the β-axis direction or in the γ-axis direction, and thereby to prevent the sensor 200 from dropping from the bag 211.

For example, the surface of the holding part 210 on the negative side thereof in the y-axis direction may include a joint part including an adhesive or the like. The holding part 210 is attached to the target part by the joint part. The joint part may include hook-and-loop fasteners. The holding part 210 may be attached to the target part by the hook-and-loop fasteners. Note that the holding part 210 may be attached to the target part by a fastener such as a hook or a snap.

Figure 4:
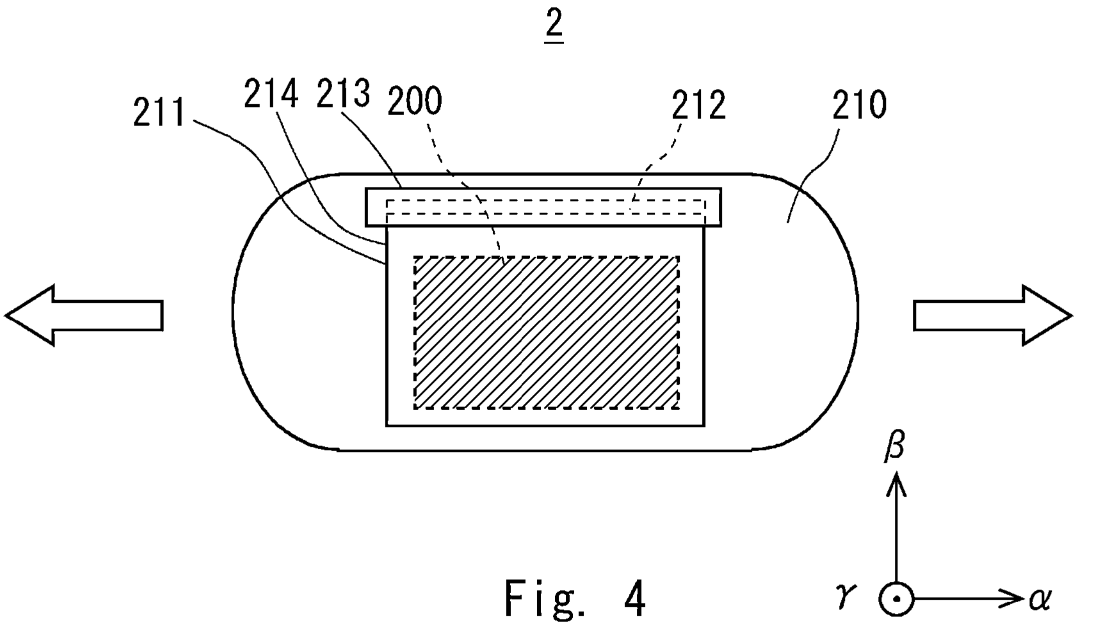
FIG. 4 is an explanatory diagram showing an example of an attaching mechanism of a sensor of a measuring instrument in the motion state monitoring system according to the first embodiment.

As shown in FIG. 4, the bag 211 may include a lid 213 that covers the insertion opening 212. That is, the bag 211 may include a storage part 214 and the lid 213. The storage part 214 is a part in which the sensor 200 is stored. The lid 213 has a rectangular shape extending along the insertion opening 212 in the α-axis direction. The part of the lid 213 on the positive side thereof in the β-axis direction is connected to the part of the bag 211 on the positive side thereof in the β-axis direction. The part of the lid 213 on the negative side thereof in the β-axis direction is opened. The lid 213 covers the insertion opening 212.

Each of the storage part 214 and the lid 213 may be formed of a stretchable member. Therefore, when the holding part 210 is attached to the target part in such a manner that the bag 211 stretches in the one direction, the lid 213 comes into close contact with the insertion opening 212. In this way, it is possible to prevent the insertion opening 212 from being opened in the β-axis direction or in the γ-axis direction, and thereby to prevent the sensor 200 from dropping from the bag 211.

Figure 5:
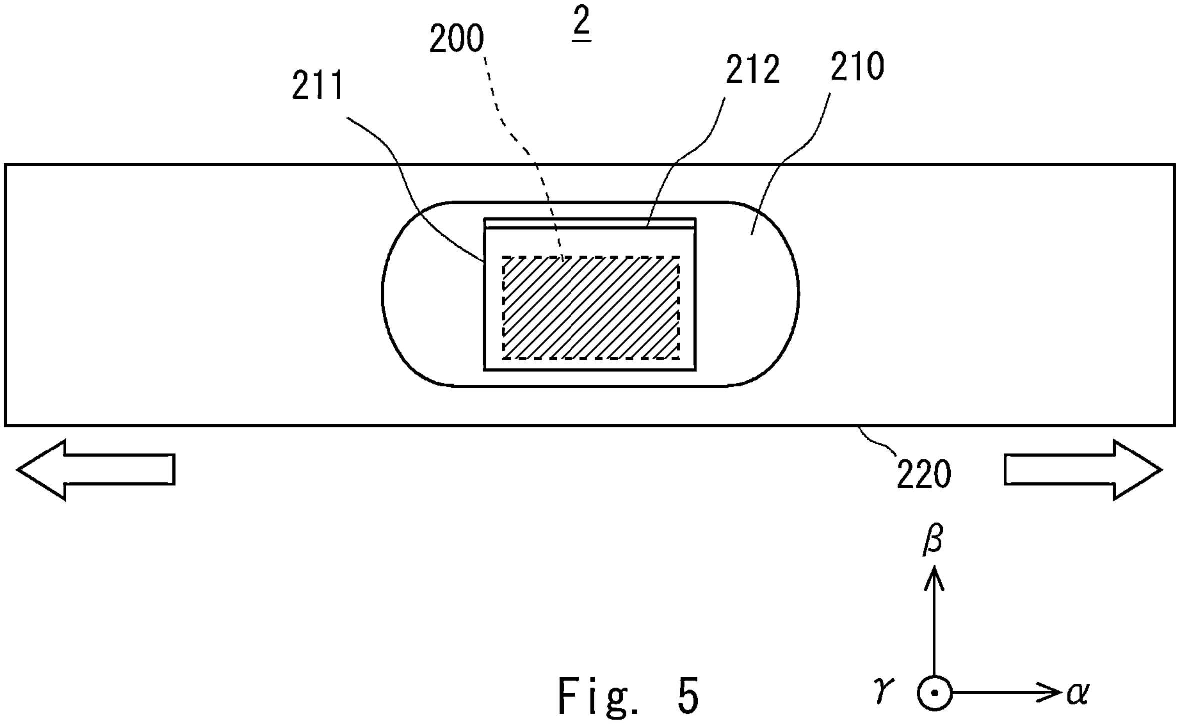
FIG. 5 is an explanatory diagram showing an example of an attaching mechanism of a sensor of a measuring instrument in the motion state monitoring system according to the first embodiment.

As shown in FIG. 5, the measuring instrument 2 (i.e., each measuring instrument 2) may further include an attaching part 220. Therefore, the measuring instrument 2 includes the sensor 200, the holding part 210, and the attaching part 220. The attaching part 220 is a member with which the sensor 200 is attached to the target part. The attaching part 220 may be called, for example, a band. The attaching part 220 has, for example, a band-like shape extending in the α-axis direction. The attaching part 220 may be formed of a stretchable member. Therefore, the attaching part 220 may include a member stretchable in the one direction. Regarding the attaching part 220, the holding part 210 is attached to a part of the attaching part 220. For example, the holding part 210 is attached to the surface of the attaching part 220 on the positive side thereof in the γ-axial direction. In this way, the holding part 210 is attached to the target part with the attaching part 220 stretchable in the one direction interposed therebetween. The holding part 210 may be attached to the attaching part 220 by the above-described joint part. The holding part 210 may be attached to the attaching part 220 by, for example, hook-and-loop fasteners. Note that the holding part 210 may be attached to the attaching part 220 by a fastener such as a hook or a snap. The attaching part 220 is attached to the target part in a state in which the attaching part 220 is stretched in the one direction. In this way, it is possible to prevent the insertion opening 212 of the holding part 210 from being opened.

Figure 6:
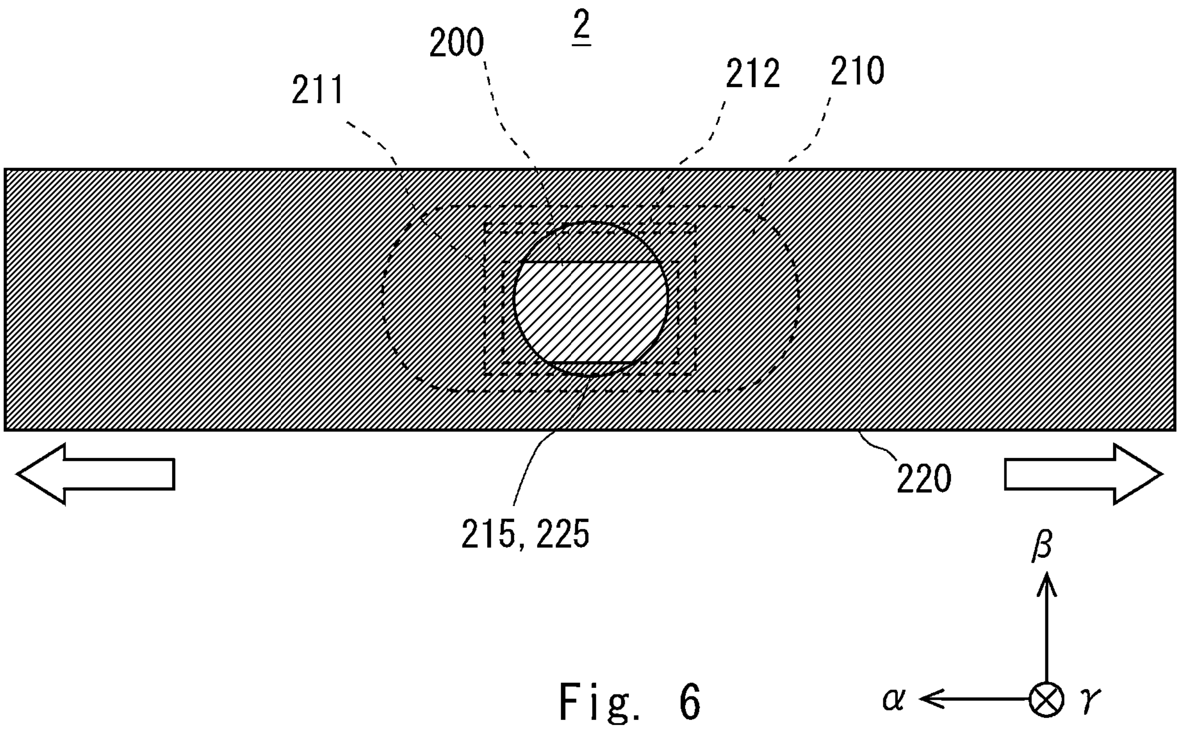
FIG. 6 is an explanatory diagram showing an example of an attaching mechanism of a sensor of a measuring instrument in the motion state monitoring system according to the first embodiment.

As shown in FIG. 6, a hole 215 and a hole 225 may be formed at parts corresponding to a predetermined position in the target part in the holding part 210 and the attaching part 220, respectively. Note that when the attaching part 220 is not provided, a hole 215 may be formed at a part corresponding to a predetermined position in the target part in the holding part 210. Each of the holes 215 and 225 may have a circular shape or a rectangular shape. The hole 215 has such a shape that the sensor 200 does not come off from the holding part 210. For example, the diameter of the hole 215 is made smaller than the length of the sensor 200. The hole 225 has such a shape that neither the sensor 200 nor the holding part 210 comes off from the attaching part 220. For example, the diameter of the hole 225 is made smaller than the length of the sensor 200 and that of the holding part 210. The holes 215 and 225 may have the same shape or different shapes.

By forming the holes 215 and 225, the sensor 200 can come into contact with the target part. In this way, the sensor 200 can perform sensing through the contact with the target part. Further, in the case where the sensor 200 performs sensing by using inspection light such as infrared light, it is possible to eliminate an obstacle or the like which would otherwise block the light, and thereby to improve the accuracy of the sensing.

The parts of the holding part 210 and the attaching part 220 located on the side thereof on which the body of the subject P is located is preferably black. Note that when the attaching part 220 is provided, only the part of the attaching part 220 located on the side thereof on which the body of the subject P is located may be black. In the case where the sensor 200 performs sensing by inspection light such as infrared light, the sensor 200 detects reflected light reflected on the target part of the subject P. Therefore, the sensor 200 preferably detects only the reflected light emitted from (i.e., reflected on) the target part. Therefore, when the part of the attaching part 220 or the like located on the side thereof on which the body of the subject P is located is black except for the hole 225, it is possible to prevent reflected light emitted from the parts other than the target part from being detected by the sensor 200.

Figure 7:
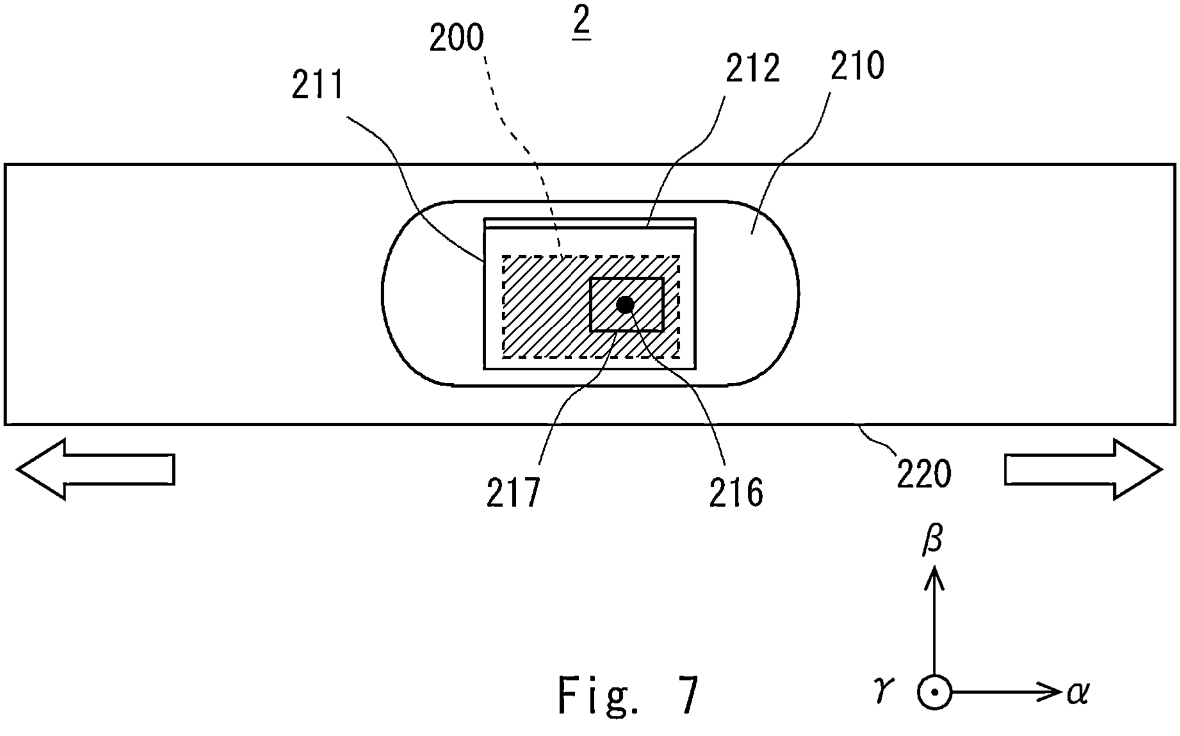
FIG. 7 is an explanatory diagram showing an example of an attaching mechanism of a sensor of a measuring instrument in the motion state monitoring system according to the first embodiment.

As shown in FIG. 7, the sensor 200 may include a light emitting unit 216. The light emitting unit 216 may include, for example, a light emitting member such as an LED (Light Emitting Diode). The light emitting unit 216 may indicate, for example, the power on and off of the sensor 200, and/or the remaining amount of electricity charged in a battery. Further, the light emitting unit 216 may indicate that sensing is in progress or that sensing has been completed. The light emitting unit 216 may indicate a predetermined state other than the above-described states and the like.

The holding part 210 may include a transparent part 217. The transparent part 217 may include, for example, a part thinner than the rest of the holding part 210. Further, the transparent part 217 may include a transparent member. The transparent part 217 may be provided in a hole, a cut-out, and the like formed in the bag 211. Further, the transparent part 217 may be provided, instead of only in a part of the bag 211, over the entire bag 211. As described above, the holding part 210 may include the transparent part 217 that lets light emitted from the light emitting unit 216 provided in the sensor 200 pass therethrough.

Since the holding part 210 includes the transparent part 217, information indicated by the sensor 200 can be reported to the user such as the subject P and a staff member.

The sensor 200 is attached to the target part with the holding part 210 or with the holding part 210 and the attaching part 220 interposed therebetween. In this way, the sensor 200 is attached to the attaching position 20 in the target part.

Figure 8:
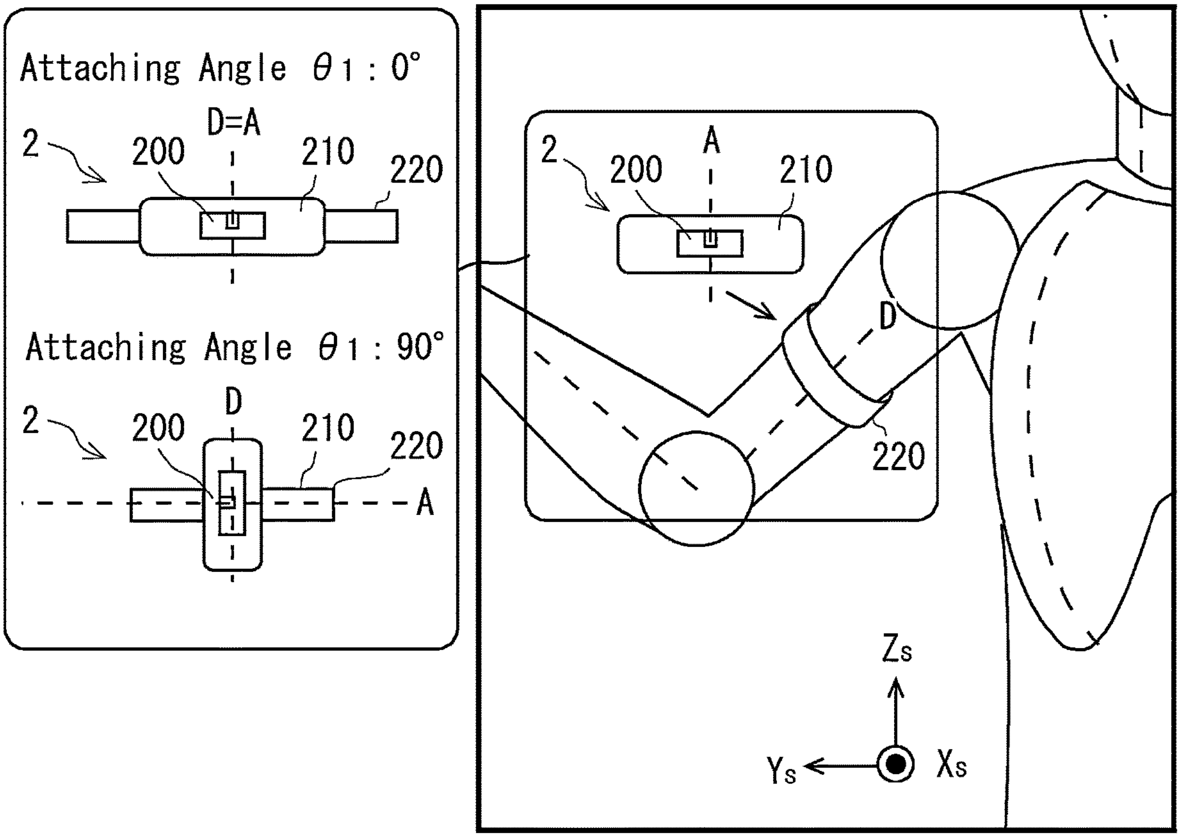
FIG. 8 shows an example of an attaching direction of a sensor in a measuring instrument in the motion state monitoring system according to the first embodiment.

The direction in which the sensor 200 is attached will be described hereinafter. FIG. 8 shows an example of a direction in which the sensor 200 is attached (hereinafter also referred to as the attaching direction of the sensor 200) in the measuring instrument 2 in the motion state monitoring system 1 according to the first embodiment. As shown in FIG. 8, the attaching direction of the sensor 200 is an attaching direction of the sensor 200 with respect to a reference direction D. In FIG. 8, the reference direction D is defined to be the axial direction of the attaching part 220 (e.g., the band) attached to the target part (e.g., the right upper arm). Further, the attaching direction indicates a relative direction of the sensor 200 with respect to the reference direction D, which is the axial direction. Specifically, the attaching direction is determined based on the angle (called the attaching angle) $\theta_1$ formed between the reference direction D and the measurement axis A of the sensor 200. The measurement axis A may be determined in advance and may be, for example, one of the α, β and γ-axes of the sensor coordinate system. For example, as shown in FIG. 8, when the attaching angle $\theta_1$ is 0°, the sensor 200 is attached so that the measurement axis A is parallel to the reference direction D. When the attaching angle $\theta_1$ is 90°, the sensor 200 is attached so that the measurement axis A is perpendicular to the reference direction D. Note that the attaching angle $\theta_1$ is not limited to 0° and 90°. As described above, the attaching direction of the sensor 200 may be an attaching direction of the sensor 200 with respect to the direction that is determined in advance according to the target part.

The reference direction D is a direction in which the attaching direction of the sensor 200 does not relatively change even when the target part is moved during the monitoring target motion. In other words, the angle (e.g., 0° or 90° as shown in FIG. 8) formed between the reference direction D and the measurement axis A of the sensor 200 does not change even when the target part is moved during the monitoring target motion. That is, the reference direction D is a direction that changes in conjunction with the absolute direction of the sensor 200 during the monitoring target motion. Note that the "absolute direction" is a direction relative to the gravity direction or the horizontal direction, and may be, for example, a direction defined in the coordinate system ($X_S$, $Y_S$, $Z_S$) for the subject P. The $X_S$-axis is a horizontal axis in the front/back direction of the subject P, and the $Y_S$-axis is a horizontal axis in the left/right direction of the subject P. Further, the $Z_S$-axis is the vertical axis in the gravity direction. Therefore, the reference direction D is a direction that changes in conjunction with the sensor 200 with respect to the absolute direction during the monitoring target motion.

Note that in this embodiment, the reference direction D can be defined according to the target part. For example, when the attaching part 220 (e.g., the band) is attached to the target part, there is a certain preferred attaching direction for each target part. For example, when the target part is an arm, the attaching part 220 is preferably attached to the arm so that its reference direction D is roughly parallel to the axial direction of the arm (i.e., the direction in which the arm extends) in view of the ease of the attaching of the attaching part 220 and the ease of the motion of the arm. Conversely, it is difficult to attach the attaching part in such a manner that the reference direction D is roughly perpendicular to the axial direction of the arm. Therefore, the axial direction of the attaching part 220 as the reference direction D can be defined in advance according to the target part. As described above, the attaching direction of the sensor 200 may be an attaching direction of the sensor 200 with respect to the axial direction of the attaching part 220 attached to the target part.

Note that although the sensor 200 is attached to the target part by using the attaching part 220 such as the band in the example shown in FIG. 8, the attaching part 220 is not indispensable. In this case (i.e., in the case where the attaching part 220 is not provided), the sensor 200 may be attached to a garment or a skin surface with the holding part 210 interposed therebetween. Even in this case, the reference direction D is a direction that is defined in advance according to the target part, such as the axial direction of the target part.

In this embodiment, the attaching mechanism (such as the holding part 210 and the attaching part 220) of the measuring instrument 2 may include a change mechanism for changing the attaching direction of the sensor 200. The change mechanism may be any mechanism capable of changing the attaching direction of the sensor 200. For example, in the case where the holding part 210 includes a joint part that can be repeatedly used, the attaching direction may be freely changed. Further, in the case where the sensor 200 is attached to the target part by using a connector between the sensor 200 and a belt or a garment, after the sensor 200 is attached so that its direction roughly coincides with the reference direction D, its attaching direction may be changed by using a knob or the like interlocked with the connector. Further, in the case where the sensor 200 is attached by using a connector having such a shape that the sensor 200 can be held in any of a plurality of attaching directions, the sensor 200 may be attached in one attaching direction selected from among the plurality of attaching directions.

Note that in this embodiment, the reference direction D can be specifically determined in advance according to the target part in the initial state, i.e., in a stationary state. FIG. 9 is a table for explaining the initial reference direction D in the motion state monitoring system 1 according to the first embodiment. As shown in FIG. 9, the absolute direction of the initial reference direction D is defined for each of plurality of target parts. In the table, the absolute direction of the initial reference direction D is expressed by using an angle $\theta_0$ formed between the reference direction D and the $Z_S$-axis. The angle $\theta_0$ may be defined based on an average human skeleton. In this embodiment, the initial reference direction D of the upper arm points outward with respect to the $Z_S$-axis, and for example, the angle $\theta_0$ of the right upper arm may be defined as 5°.

Further, the initial reference direction D of the forearm points further outward with respect to the $Z_S$-axis than the upper arm does, and for example, the angle $\theta_0$ of the right forearm may be defined as 10°. Note that an angle $\theta_0$ for each part may be defined for each subject P based on his/her attribute information such as his/her age, gender, height, or weight.

As descried above, even when the initial reference direction D changes according to the target part, the initial reference direction D may be specifically defined. Therefore, at least the initial attaching direction can be converted into an absolute direction which is a univocal index for the subject P.

The sensor 200 according to this embodiment is configured so that its attaching direction can be changed. Therefore, since the user can freely set the attaching direction of the sensor 200, its useability can be improved. Further, depending on the sensor 200, the accuracy of the measurement result can be improved by setting the sensor 200 in a suitable direction.

Hereinafter, the attaching direction with respect to the reference direction D is simply referred to as the "attaching direction".

Figure 10:
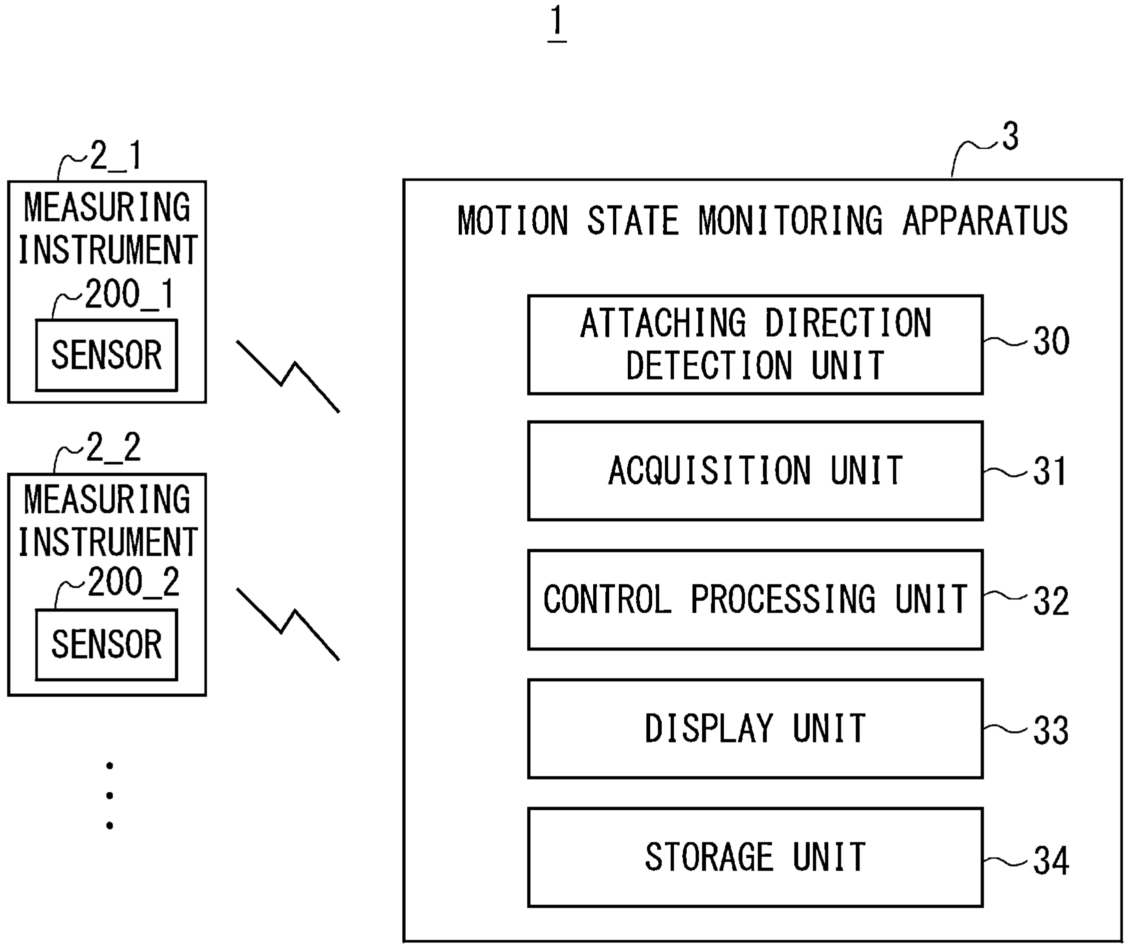
FIG. 10 is a block diagram showing an example of a measuring instrument and a motion state monitoring apparatus in the motion state monitoring system according to the first embodiment.

FIG. 10 is a block diagram showing an example of the measuring instruments 2 and the motion state monitoring apparatus 3 in the motion state monitoring system 1 according to the first embodiment. As described above, the motion state monitoring system 1 includes the measuring instruments 2 and the motion state monitoring apparatus 3. The measuring instrument 2 (i.e., each measuring instrument 2) includes a sensor 200. In the drawing, the sensors 200 are, among the prepared sensors 200-1 to 200-11, sensors 200 associated with the attaching positions 20 selected based on the monitoring target motion. It is assumed that the sensors 200 have been paired with the motion state monitoring apparatus 3 and calibrated in advance. Note that the number of sensors 200 is not limited to one, but may be two or more.

The motion state monitoring apparatus 3 includes an attaching direction detection unit 30, an acquisition unit 31, a control processing unit 32, a display unit 33, and a storage unit 34. The attaching direction detection unit 30, the acquisition unit 31, the control processing unit 32, the display unit 33, and the storage unit 34 function as attaching direction detection means, acquisition means, control processing means, display means, and storage means, respectively.

The attaching direction detection unit 30 detects the attaching direction of the sensor 200 (e.g., each sensor 200). As described above, the attaching direction of the sensor 200 may be an attaching direction of the sensor 200 with respect to a direction that is determined in advance according to the target part, or an attaching direction of the sensor 200 with respect to the axial direction of the attaching part 220 attached to the target part.

Specifically, the attaching direction detection unit 30 may detect the attaching direction of the sensor 200 based on the output of the sensor 200 when the sensor 200 is attached to the target part. In this case, the attaching direction detection unit 30 calculates the attaching angle with respect to the $Z_S$-axis based on information about the $Z_S$-axis acquired from the sensor 200 at the time of the calibration and angle information of the sensor 200 in a period between the stationary state in the calibration and the attaching thereof. In this way, the attaching direction detection unit 30 can detect the attaching direction of the sensor 200.

Further, for example, the attaching direction detection unit 30 may include, for each sensor 200, an attaching direction detection sensor and an attaching direction detecting mechanism separately disposed near that sensor 200. Further, the attaching direction detecting mechanism may be configured so that an electric current flows according to the angle between the measurement axis A of the sensor 200 and the reference direction D. The attaching direction detection sensor detects this electric current. In this way, the attaching direction is detected according to the detected magnitude of the electric current. Note that when the attaching part 220 such as a band is used for attaching the sensor 200, the attaching direction detection sensor and the attaching direction detecting mechanism may be disposed in the attaching part 220. Further, the attaching direction detection sensor and the attaching direction detecting mechanism may be included in the measuring instrument 2. The attaching direction detection unit 30 may acquire information about the attaching direction based on the output from the attaching direction detection sensor.

Further, for example, the attaching direction detection unit 30 may detect the attaching direction of the sensor 200 based on a photographed image of the attached sensor 200. For example, the attaching direction detection unit 30 may include an attaching direction detection camera disposed in front of, behind, or above the subject P. Then, the attaching direction detection unit 30 may detect the attaching direction of the sensor 200 by photographing the sensor 200 and performing image processing such as pattern matching on the photographed image. Note that the attaching direction detection camera may be included in the measuring instrument 2, and the attaching direction detection unit 30 may acquire an image from the attaching direction detection camera and acquire information about the attaching direction based on the acquired image.

Further, in the case where the attaching direction of the sensor 200 can be adjusted by a knob or the like interlocked with the connector, the attaching direction detection unit 30 may detect the attaching direction based on the amount of the movement of the knob.

In this embodiment, the attaching direction detection unit 30 detects the attaching direction of the sensor 200 in the initial state, i.e., in a stationary state just before the measurement. Then, the attaching direction detection unit 30 supplies the detected information about the detected attaching direction to the control processing unit 32.

The acquisition unit 31 acquires sensing information of the sensor 200 attached to the target part. In this embodiment, the acquisition unit 31 receives and acquires the sensing information from the sensor 200. However, the acquisition of sensing information is not limited to such an example, and the acquisition unit 31 may indirectly acquire the sensing information from an external computer (not shown) that holds the sensing information. The acquisition unit 31 supplies the acquired sensing information to the control processing unit 32.

The control processing unit 32 controls each component of the sensors 200 and the motion state monitoring apparatus 3. Further, the control processing unit 32 performs a tagging process for associating the attaching direction of the sensor 200 with sensing-related information obtained in the attaching direction. Then, the control processing unit 32 outputs, to an output unit such as the display unit 33, the sensing-related information, which has undergone the tagging process, in association with the attaching direction of the sensor 200. Further, the control processing unit 32 may store the sensing-related information, which has undergone the tagging process, in the storage unit 34.

Further, the control processing unit 32 may output sensing-related information by using an algorithm obtained by performing machine learning using attaching directions and sensing-related information as learning data. Specifically, the control processing unit 32 may, for example, train an algorithm in advance through machine learning by using attaching directions and sensing-related information associated with the attaching directions as learning data. Then, by using this algorithm, the control processing unit 32 may output, based on an input attaching direction or input sensing-related information, sensing-related information different from the input sensing-related information.

The display unit 33 is an example of the output unit and is a display device that displays the sensing-related information supplied from the control processing unit 32. In this embodiment, the display unit 33 may be a touch panel formed together with an input unit (not shown). Note that the output unit may include, in place of the display unit 33 or in addition to the display unit 33, an audio output unit that outputs sensing-related information by voice or sound, a data output unit that outputs sensing-related information in a predetermined data format, a transmitting unit that transmits sensing-related information to an external server, or the like.

The storage unit 34 includes a storage medium that stores information necessary for various types of processing performed by the motion state monitoring apparatus 3. The storage unit 34 may store the sensing-related information, which has undergone the tagging process. However, when the output unit includes a transmitting unit, the storage unit 34 does not necessarily have to store the sensing-related information.

Figure 11:
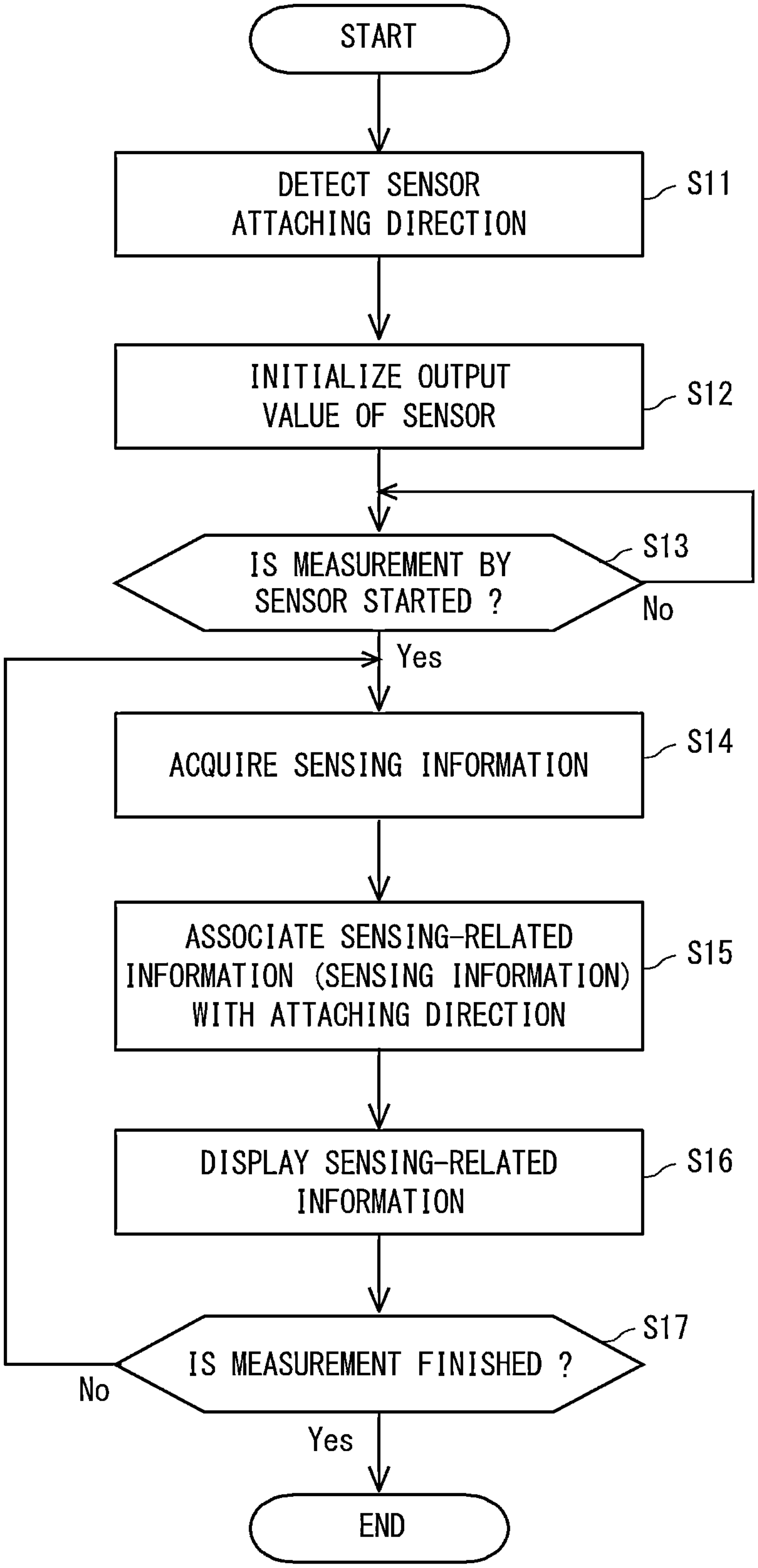
FIG. 11 is a flowchart showing an example of a motion state monitoring method using the motion state monitoring system according to the first embodiment.
Figure 12:
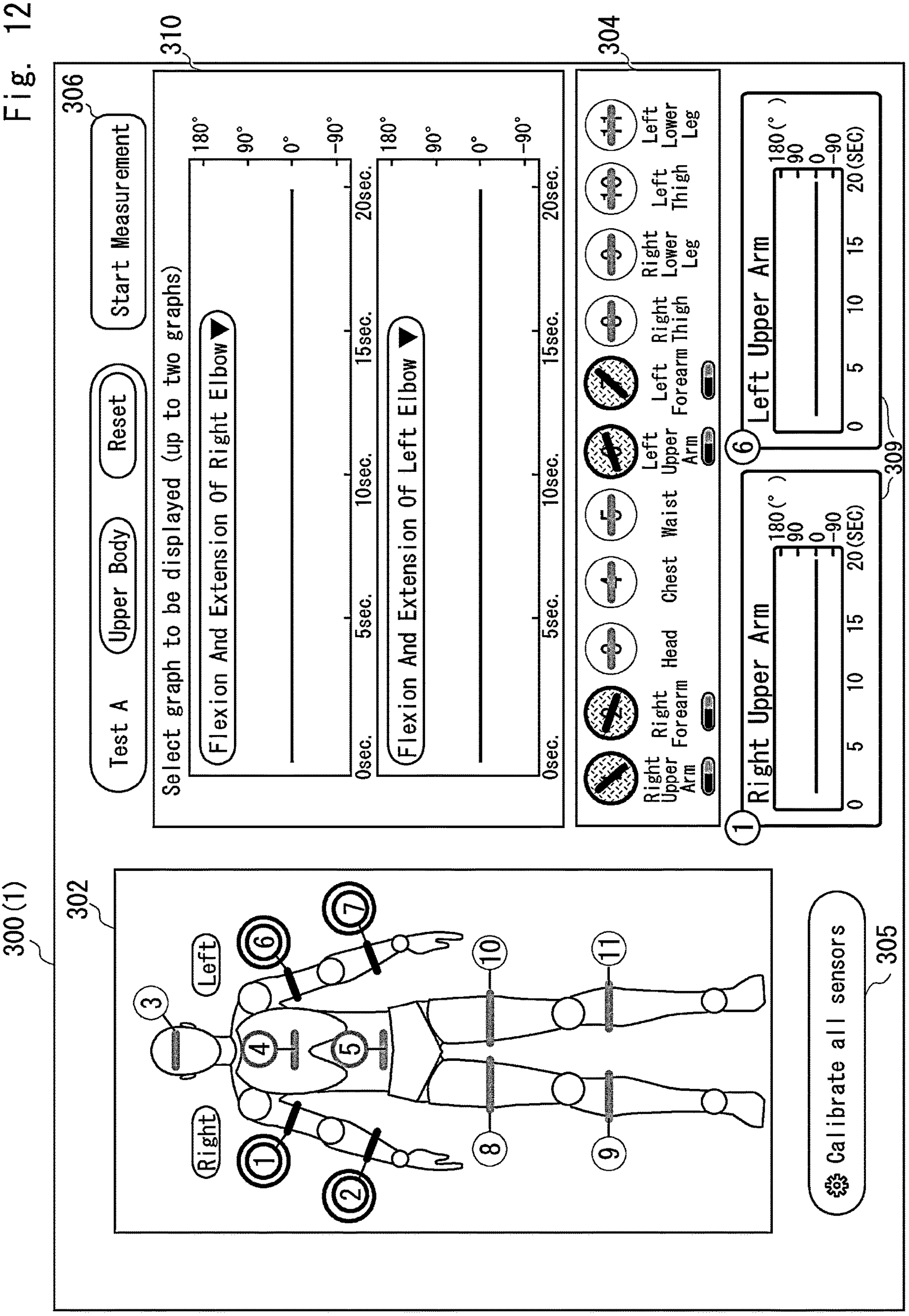
FIG. 12 shows an example of a display screen of a display unit before the start of measurement in the motion state monitoring system according to the first embodiment.
Figure 13:
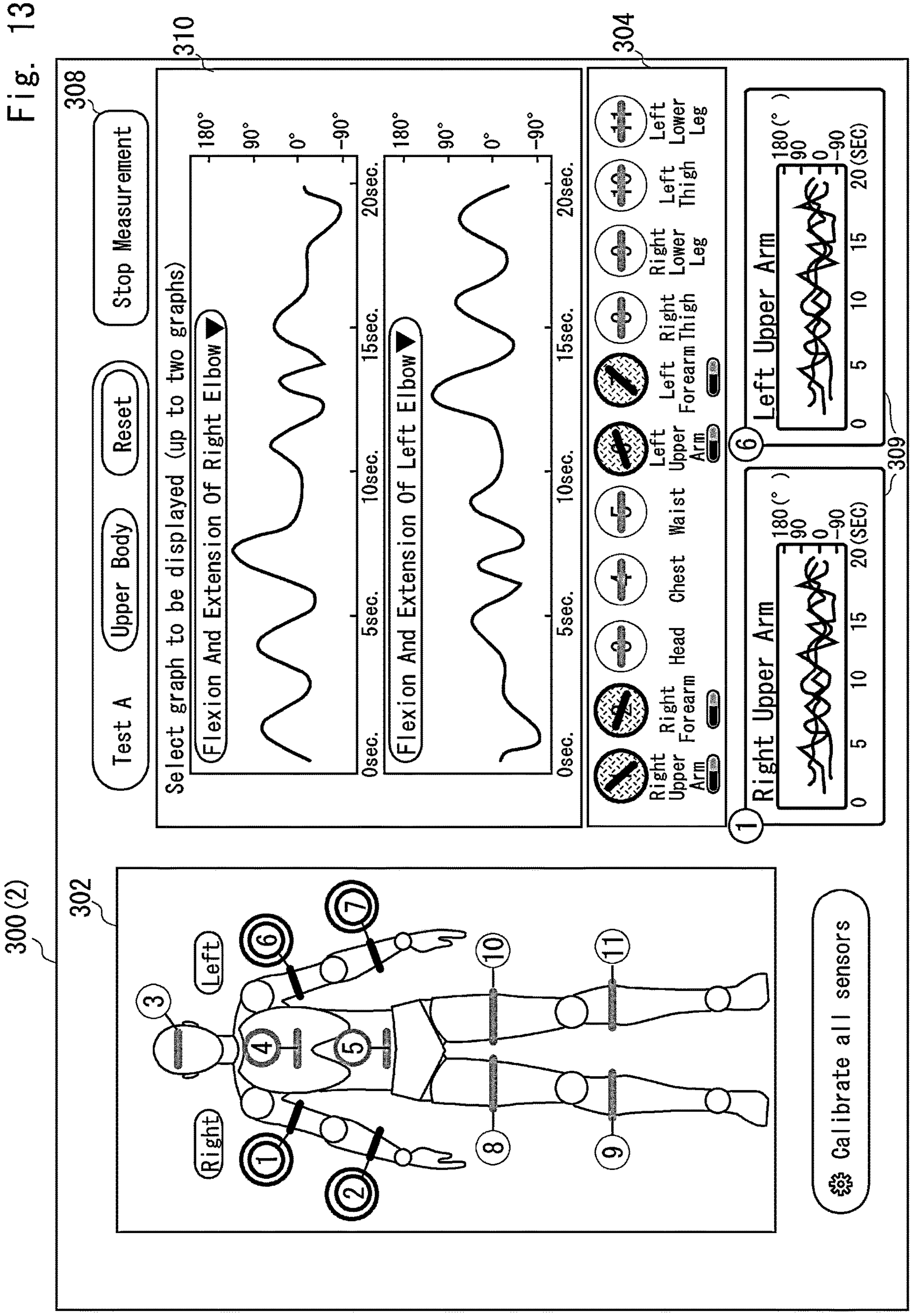
FIG. 13 shows an example of a display screen of the display unit at the end of the measurement in the motion state monitoring system according to the first embodiment.

Next, a motion state monitoring method according to the first embodiment will be described. FIG. 11 is a flowchart showing an example of a motion state monitoring method using the motion state monitoring system 1 according to the first embodiment. FIG. 12 shows an example of a display screen of the display unit 33 before the start of measurement in the motion state monitoring system 1 according to the first embodiment. FIG. 13 shows an example of a display screen of the display unit 33 at the end of the measurement in the motion state monitoring system 1 according to the first embodiment.

The steps shown in FIG. 11 start when: a monitoring target motion is selected by a user; attaching positions 20 are determined based on the selected monitoring target motion; and then sensors 200 are respectively attached at the determined attaching positions 20 corresponding to the selected monitoring target motion. Note that in the below-shown example, the control processing unit 32 handles (i.e., regards) the sensing information as the sensing-related information.

Firstly, as shown in a step S11, the attaching direction detection unit 30 in the motion state monitoring apparatus 3 detects the attaching direction of the sensor 200 (e.g., each sensor 200) in response to the situation that the subject P and the sensors 200 become a stationary state.

Next, as shown in a step S12, the control processing unit 32 initializes the output value of the sensor 200 (e.g., each sensor 200). Specifically, the control processing unit 32 corrects the output value of the sensor 200 in the stationary state just before the measurement to zero. There are cases where even though the sensor 200 is calibrated, the output error such as a drift error cannot be adjusted to zero, and the error increases over the elapsed time. Accordingly, the output error in the period from the start of the measurement to the end thereof can be minimized by the above-described step. However, when the output error is negligible, the above-described step may be skipped.

Next, as shown in a step S13, the control processing unit 32 determines whether or not to start the measurement by the sensors 200. In a step S13, when the control processing unit 32 starts the measurement by the sensors 200 (in the case of Yes), the process proceeds to a step S14. On the other hand, in the step S13, when the control processing unit 32 does not start the measurement by the sensors 200 (in the case of No), the process in the step S13 is repeated.

Note that as shown in FIG. 12, a display image 300(1) before the start of the measurement displayed by the display unit 33 is shown. The display image 300(1) includes a plurality of display areas, i.e., a display area 302, a display area 304, a display area 305, a display area 306, a display area 309, and a display area 310.

In the display area 302, a plurality of icon images representing respective attaching positions 20 that are candidates for positions where the sensors 200 are attached. In the display area 302, the attaching positions 20 corresponding to the selected measurement motion (positions indicated by "1", "2", "6" and "7" in the drawing) may be highlighted. In this way, the user can easily visually recognize the attaching positions 20, so that he/she can smoothly carry out the motion test.

Note that when the user clicks on an icon image representing an attaching position 20 (e.g., one of the attaching positions) in the display area 302, an image (not shown) indicating the attaching direction of the sensor 200 associated with this attaching position 20 is displayed. Therefore, the user can easily understand the attaching direction of each sensor 200 through this image.

In the display area 304, the rotation angle of each of the sensors 200-1, 200-2, . . . , and 200-11 associated with the respective attaching positions 20-1, 20-2, . . . , and 20-11 is displayed in a two-dimensional manner. Note that the displayed rotation angles dynamically change in response to the motions of the sensors 200 in conjunction with the motion of the subject P. Therefore, the user can specify a sensor(s) 200 that is turned off or a sensor(s) 200 that is not properly operating through the display area 304 before the start of the measurement.

Alternatively, the attaching directions of the sensors 200-1, 200-2, . . . , and 20-11 associated with the respective attaching positions 200-1, 20-2, . . . , and 20-11 may be visually displayed in the display area 304. Therefore, the user can intuitively understand the attaching direction of each sensor 200 through the display area 304.

In the display area 305, an input operation button for, when a plurality of sensors 200 are used for the motion test, calibrating the plurality of sensors 200 at once is displayed. In this way, the user can easily request the calibration of each of the plurality of sensors 200 through the display area 305.

In the display area 306, an input operation button for starting the motion test, i.e., starting the measurement by the sensors 200, is displayed. In this way, the user can easily request to start the measurement by the sensors 200 through the display area 306.

In the display area 309, sensing-related information of each of used sensors 200 is displayed. Any sensing-related information has not been displayed yet because the measurement has not started yet. In the display area 310, motion state indices of the target parts are displayed for each performed monitoring target motion. Any motion state index of any of the target parts has not been displayed yet because the measurement has not started yet.

Then, as shown in a step S14 shown in FIG. 11, the control processing unit 32 acquires sensing information from the sensors 200 through the acquisition unit 31.

Next, as shown in a step S15, the control processing unit 32 uses the sensing information as sensing-related information, and attaches (i.e., assigns), as tags, information about the attaching directions of the sensors 200 to the sensing-related information. In this way, the attaching directions and the sensing-related information can be associated with each other.

Next, as shown in a step S16, the control processing unit 32 supplies the sensing-related information, which has undergone the tagging process, to the display unit 33, and thereby makes the display unit 33 display the sensing-related information.

Next, as shown in a step S17, the control processing unit 32 determines whether or not to finish the measurement by the sensors 200. In the step S17, when the control processing unit 32 finishes the measurement (in the case of Yes), the process is finished. On the other hand, when the control processing unit 32 does not finish the measurement in the step S17 (in the case of No), the process is returned to the step S14.

Note that in the above-described example, the motion state monitoring apparatus 3 determines whether or not to start the measurement by the sensors 200 in the step S13 after the process in the step S12 is finished. However, the motion state monitoring apparatus 3 may instead perform the process in the step S12 in response to, after the process in the step S11, the determination that the measurement by the sensors 200 should be started (Yes in Step S13). In this case, the control processing unit 32 may proceed to the step S14 after the process in the step S12 is performed or in parallel with the execution of the process in the step S12. Further, when the motion state monitoring apparatus 3 does not start the measurement by the sensors 200 (No in Step S13), the process in the step S13 may be repeated.

Further, although the motion state monitoring apparatus 3 uses the sensing information as the sensing-related information in the above-described example, the motion state monitoring apparatus 3 may use sensing information that has been subjected to various conversion processes instead of or in addition to the aforementioned sensing information. These conversion processes may include a conversion process from quaternion information into rotation angles around the X, Y and Z-axes. The rotation angle around the $X_S$-axis indicates a roll angle, and the rotation angle around the $Y_S$-axis indicates a pitch angle. Further, the rotation angle around the $Z_S$-axis indicates a yaw angle. The control processing unit 32 calculates the rotation angles around the X, Y and Z-axes in the sensor coordinate system by using the quaternion information, and thereby converts them into yaw, roll and pitch angles, respectively. Further, this conversion process may include a normalization process, a standardization process, or a synthesizing process of a graph. In this case, the control processing unit 32 may attach, as tags, information about the attaching directions of the sensors 200 to the sensing information, which has undergone the conversion process, instead of or in addition to the process in the step S15, and may associate the attaching directions with the sensing information, which has undergone the conversion process.

FIG. 13 shows a display image 300(2) at the end of the measurement displayed by the display unit 33. Similarly to the display image (1), the display image 300(2) includes a plurality of display areas, i.e., a display area 302, a display area 304, a display area 305, a display area 306, a display area 309, and a display area 310. The display areas 302 and 304 on the display image 300(2) are similar to the display areas 302 and 304 on the display image 300(1) shown in FIG. 12.

The attaching direction of each of the used sensors 200 may be displayed near an icon image representing a respective one of the attaching positions 20 in the display area 302, or may be displayed in response to clicking on the icon image performed by the user. In this way, the user can intuitively understand the attaching directions of the used sensors 200.

In the display area 308, an input operation button for terminating the motion test, i.e., stopping measurement by the sensors 200, is displayed. In this way, the user can easily request to stop the measurement by the sensors 200 through the display area 308.

In the display area 309, sensing-related information for each of the used sensors 200 is displayed. The rotation angles around the $X_S$, $Y_S$ and $Z_S$-axes, which have been determined based on the outputs of some of the sensors among the used sensors 200-1, 200-2, 200-6, and 200-7, i.e., the outputs of the sensors 200-1 and 200-6, are displayed in a chronological order. Therefore, the display area 309, together with the display area 304, outputs the sensing-related information associated with the attaching directions of the used sensors 200 in the form of the display described above, so that it is possible to enable the user to understand the attaching conditions and the measurement results under the attaching conditions in association with each other. In this way, the user can analyze, evaluate, or use the measurement results while distinguishing them from one another according to the attaching condition.

In the display area 310, motion state indices of the target parts are displayed for each performed monitoring target motion. The motion state index is an index indicating the motion state of the target part when the monitoring target motion is performed. The control processing unit 32 calculates the motion state index of the target part based on the sensing-related information of the sensor 200. For example, when the monitoring target motion is "flexion and extension of right elbow", the sensing-related information of each of the sensors 200-1 and 200-2 at the attaching positions 20-1 and 20-2, respectively, is used. In this case, the control processing unit 32 may calculate the motion state index based on the difference between the sensing-related information of the sensor 200-1 and that of the sensor 200-2. Specifically, the control processing unit 32 calculates three-dimensional rotation angles as the motion state index based on the difference between the quaternion information of the sensors 200-1 and that of the sensor 200-2. In this case, the control processing unit 32 calculates the rotation angles in the order of Z-axis→Y-axis→X-axis, and converts them to the rotation angles around the $X_S$, $Y_S$ and $Z_S$-axes. Note that the order of calculations of rotation angles may be determined in advance according to the monitoring target motion. In the display area 310, the motion state indices of some of the plurality of performed monitoring target motions are displayed in a chronological order.

According to this embodiment, in the measuring instrument 2 (i.e., each measuring instrument 2), the holding part 210 includes the bag 211 formed of a stretchable member. The bag 211 includes an insertion opening extending in one direction. When the holding part 210 holding the sensor 200 in the bag 211 is attached to the target part, the holding part 210 may be attached to the target part in such a manner that the bag 211 stretches in the one direction. In this way, it is possible to reduce the time taken to attach the sensor 200 (e.g., each sensor 200) and prevent the sensor 200 from being dropped.

The bag 211 may include the lid 213 that covers the insertion opening 212. In this way, it is possible to prevent the sensor 200 from being dropped more effectively. The holding part 210 may be attached to the target part with the attaching part 220 stretchable in the one direction interposed therebetween. In this way, the attaching direction of the sensor 200 can be fixed.

The motion state monitoring system 1 outputs the attaching directions of the sensors 200 and the measurement results thereof in association with each other. Therefore, the motion state monitoring system 1 can appropriately manage the measurement results according to the attaching directions of the sensors 200, so that its usability is improved.

Further, the motion state monitoring system 1 automatically detects the initial attaching direction of the sensor 200 (e.g., each sensor 200). Therefore, it is possible to suitably set the attaching directions of the sensors when they are attached to the target parts according to the preference of the subject P or a staff member, and to easily associate such settings with measurement results obtained under the settings.

Second Embodiment

Next, a second embodiment will be described. This embodiment is characterized in that arithmetic processing according to the attaching direction is performed on a measurement result. Since the configuration and functions of a motion state monitoring system 1 according to the second embodiment are similar to those of the motion state monitoring system 1 according to the first embodiment, descriptions thereof will be omitted.

The control processing unit 32 of the motion state monitoring system 1 performs arithmetic processing according to the attaching direction on sensing information or sensing-related information. The aforementioned arithmetic processing may be, for example, arithmetic processing for, when the sensing-related information changes according to the attaching direction, cancelling out or suppressing the influence of the attaching direction even when the target part is moved in the same manner in the same monitoring target motion. In particular, when the control processing unit 32 calculates the rotation angles around the X, Y and Z-axes by using quaternion information and converts them into the rotation angles around the $X_S$, $Y_S$ and $Z_S$-axes, it is necessary to convert four-dimensional vector data into three-dimensional data. In this calculation process, there is a problem that the obtained rotation angles change depending on the order in which the rotation angles around the respective axes are calculated, and hence the results cannot be correctly compared. In order to suppress such an influence, it is preferable to determine the order in which the rotation angles are calculated in advance. Note that the preferred order in which the rotation angles are calculated depends on the attaching direction of the sensor 200, so it is effective to determine the order in which the rotation angles are calculated according to the attaching direction of the sensor 200 in advance.

Therefore, in the motion state monitoring system 1, the control processing unit 32 perform the arithmetic processing by using an arithmetic processing table 320 in which arithmetic processing modes according to the attaching direction are defined. Then, the control processing unit 32 outputs the result of the arithmetic processing to the output unit in association with the initial attaching direction of the sensor 200.

FIG. 14 shows an example of the data structure of the arithmetic processing table 320 used by the control processing unit 32 in the motion state monitoring system 1 according to the second embodiment. As shown in FIG. 14, the arithmetic processing table 320 is a table in which attaching angles $\theta_1$ and orders of calculations of rotation angles are associated with each other. In the arithmetic processing table 320, for example, when the attaching angle $\theta_1$ is 0°, it is specified that the rotation angles around the respective axes are calculated in the order of X-axis→Z-axis→Y-axis. Further, in the arithmetic processing table 320, when the attaching angle $\theta_1$ is 90°, it is specified that the rotation angles around the respective axes are calculated in the order of Y-axis→Z-axis→X-axis. By referring to the arithmetic processing table 320, the control processing unit 32 can easily perform suitable arithmetic processing according to the attaching direction.

Note that the order of calculations of rotation angles is determined according to the attaching direction of the sensor 200 in the arithmetic processing table 320. However, the order of calculations of rotation angles may be instead determined according to the attaching direction and the target part or the monitoring target motion.

Further, the arithmetic processing table 320 may include a calculation parameter used for the arithmetic processing instead of or in addition to the order of calculations of rotation angles. In this case, the calculation parameter may be a constant determined according to the attaching angle $\theta_1$, or may include a predetermined function using the attaching direction $\theta_1$ as a variable.

As described above, according to the second embodiment, the control processing unit 32 can easily compare and use a plurality of measurement results irrespective of the attaching direction of the sensor 200. Note that the second embodiment provides effects similar to those obtained in the first embodiment.

Third Embodiment

Next, a motion state monitoring system according to a third embodiment will be described. This embodiment is characterized in that the attaching direction of the sensor 200 is detected not only in the initial stage but also during the monitoring target motion. Since the configuration and functions of a motion state monitoring system 1 according to the third embodiment are similar to those of the motion state monitoring systems according to the first and second embodiments, descriptions thereof will be omitted. However, in the motion state monitoring system 1 according to the third embodiment, the attaching direction detection unit 30 detects the attaching direction during the measurement by the sensor 200 in addition to in the initial stage. Further, in the motion state monitoring system 1, the control processing unit 32 outputs, in response to the detection of an event in which the attaching direction changes during the measurement by the sensor 200, sensing-related information obtained after the event in association with the attaching direction after the event.

Figure 15:
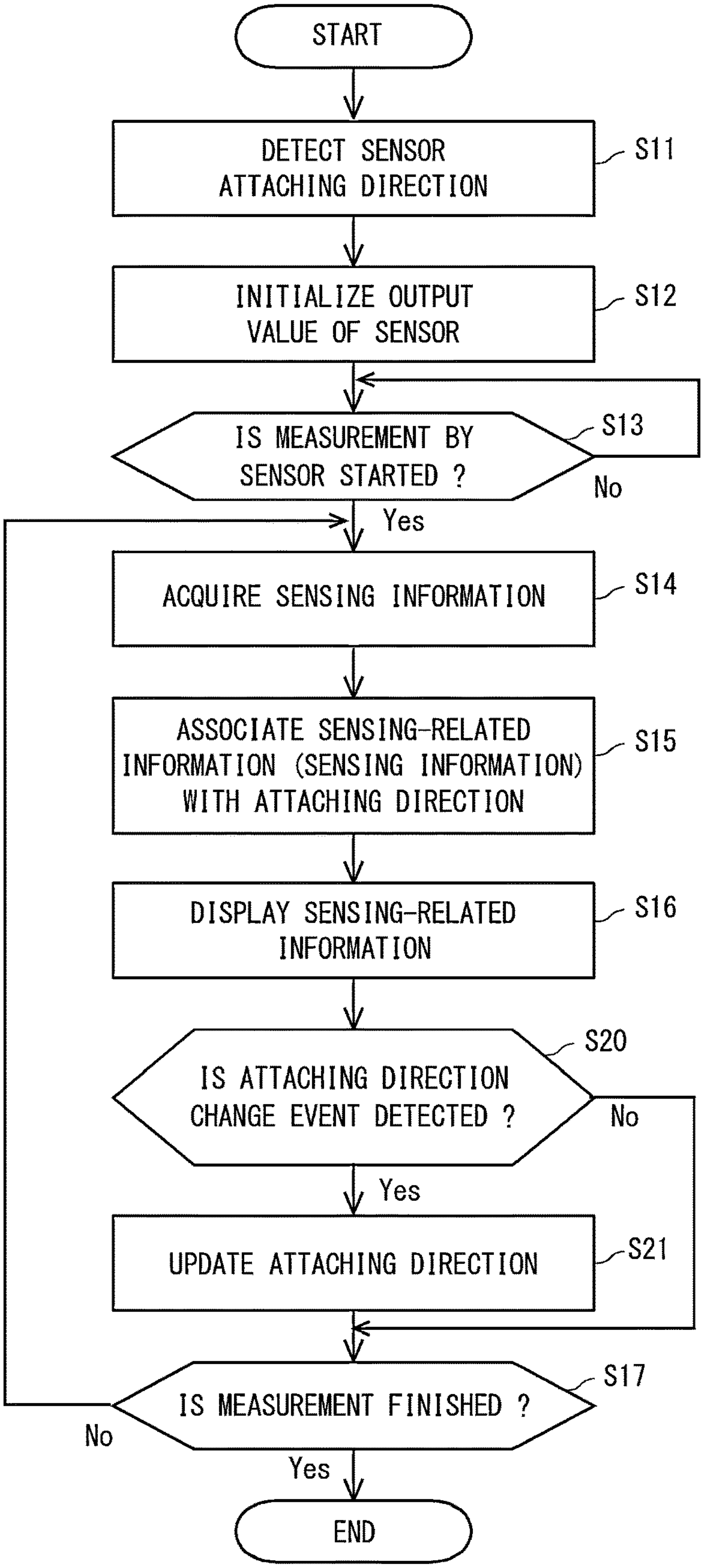
FIG. 15 is a flowchart showing an example of a motion state monitoring method using a motion state monitoring system according to a third embodiment.

FIG. 15 is a flowchart showing an example of a motion state monitoring method using the motion state monitoring system 1 according to the third embodiment. The steps shown in FIG. 15 include steps S20 and S21 in addition to the steps shown in FIG. 11. Note that steps similar to those shown in FIG. 11 are assigned the same symbols, and descriptions thereof are omitted.

In a step S16, in response to the display of sensing-related information by the display unit 33, the attaching direction detection unit 30 determines whether or not an event in which the attaching direction has changed is detected as shown in the step S20. In the step S20, for example, when the subject P has intentionally changed the attaching direction during the monitoring target motion, or when the attaching direction of the sensor 200 has been unintentionally changed during the monitoring target motion, it is detected as an event in which the attaching direction has changed.

Specifically, when a difference between, for example, a previous attaching direction and a current attaching direction, i.e., a difference between, for example, a previously-measured attaching angle $\theta_1$ and a currently-measured attaching angle $\theta_1$, is equal to or larger than a predetermined threshold, the attaching direction detection unit 30 may determine that it has detected an event in which the attaching direction has changed. A method similar to the method for detecting the initial attaching direction may be used for the detection of the attaching direction in the above-described process.

Alternatively, the attaching direction detection unit 30 may instead detect an event in which the attaching direction has changed based on a change in the sensing-related information over time. For example, the attaching direction detection unit 30 may determine that an event in which the attaching direction has changed is detected when a discontinuous change equal to or larger than a predetermined threshold is detected in time-series information of the sensing-related information. Whether or not there is a discontinuous change may be determined by determining whether or not a difference between, for example, previous sensing-related information and current sensing-related information is equal to or larger than a predicted value by a predetermined threshold or larger.

In a step S20, when it is determined that the attaching direction detection unit 30 has detected an event in which the attaching direction has changed (in the case of Yes), the process proceeds to the step S21. On the other hand, when it is not determined that the attaching direction detection unit 30 has detected an event in which the attaching direction has changed in the step S20 (in the case of No), the process proceeds to the step S17.

In the step S21, the control processing unit 32 updates the attaching direction of the sensor 200 associated with the sensing-related information to the attaching direction obtained after the change event. Then, the control processing unit 32 advances the process to the step S17.

As described above, according to the third embodiment, the motion state monitoring system 1 detects a change in the attaching direction of the sensor 200 during the measurement, and outputs the changed attaching direction in association with the sensing-related information. Therefore, even when the attaching direction is changed intentionally or unintentionally in the middle of the monitoring target motion, the motion state monitoring system 1 can manage the subsequent measurement results in association with the changed attaching direction. Note that the third embodiment provides effects similar to those obtained in the first and second embodiments.

Note that the present disclosure is not limited to the above-described embodiments, and they can be modified as appropriate without departing from the scope and spirit of the disclosure. Examples of other embodiments include the following embodiments.

Other First Embodiment

In the first embodiment, the control processing unit 32 in the motion state monitoring system 1 outputs sensing-related information in association with the relative attaching direction of the sensor 200 with respect to the reference direction D. However, the control processing unit 32 may convert a relative attaching direction detected from the user into an absolute direction, and output sensing-related information in association with the absolute direction instead of or in addition to the relative attaching direction.

For example, the control processing unit 32 can calculate the attaching angle $\theta_1'$ between the measurement axis A and the $Z_S$-axis in the initial stage by adding the angle $\theta_0$ between the initial reference direction D and the $Z_S$-axis shown in FIG. 9 to the detected initial attaching direction $\theta_1$ of the sensor 200. Then, the control processing unit 32 outputs, as information indicating the absolute direction of the sensor 200 in the initial stage, the attaching angle $\theta_1'$ in the initial stage in association with the sensing-related information. Note that the absolute direction of the sensor 200 during the measurement can be calculated based on the absolute direction of the sensor 200 in the initial stage, the rotation angle of the sensor 200, which is the measurement result of the sensor 200, and the amount of change in the attaching angle during the measurement. In this way, the user can analyze the measurement result while taking more detailed measurement conditions into consideration, and hence the accuracy of the analysis is improved.

Other Second Embodiment

In the second embodiment, the control processing unit 32 in the motion state monitoring system 1 performs arithmetic processing according to the attaching direction on the sensing information or the sensing-related information. However, instead of or in addition to this process, the control processing unit 32 may perform arithmetic processing according to the above-described absolute direction of the sensor 200 on the sensing information or the sensing-related information. In this case, in the arithmetic processing table 320, the attaching angle $\theta_1'$ described above in the second other embodiment may be associated with the calculation parameter of the arithmetic processing determined according to the attaching angle $\theta_1'$. In this way, the control processing unit 32 can easily compare and use measurement results irrespective of the direction of the sensor 200.

Although the present disclosure has been described as a hardware configuration in the above embodiments, the present disclosure is not limited to this. According to the present disclosure, each of the processing related to the motion state monitoring method can be implemented by causing the processor to execute a computer program, for example, a motion state monitoring program.

In the embodiments described above, the computer is composed of a computer system including a personal computer, a word processor, etc. However, the computer is not limited to this and may be constituted by a LAN server, a host of computer (personal computer) communication, a computer system connected to the Internet, or the like. The functions may be distributed to devices on the network and a whole network may serve as a computer.

Figure 16:
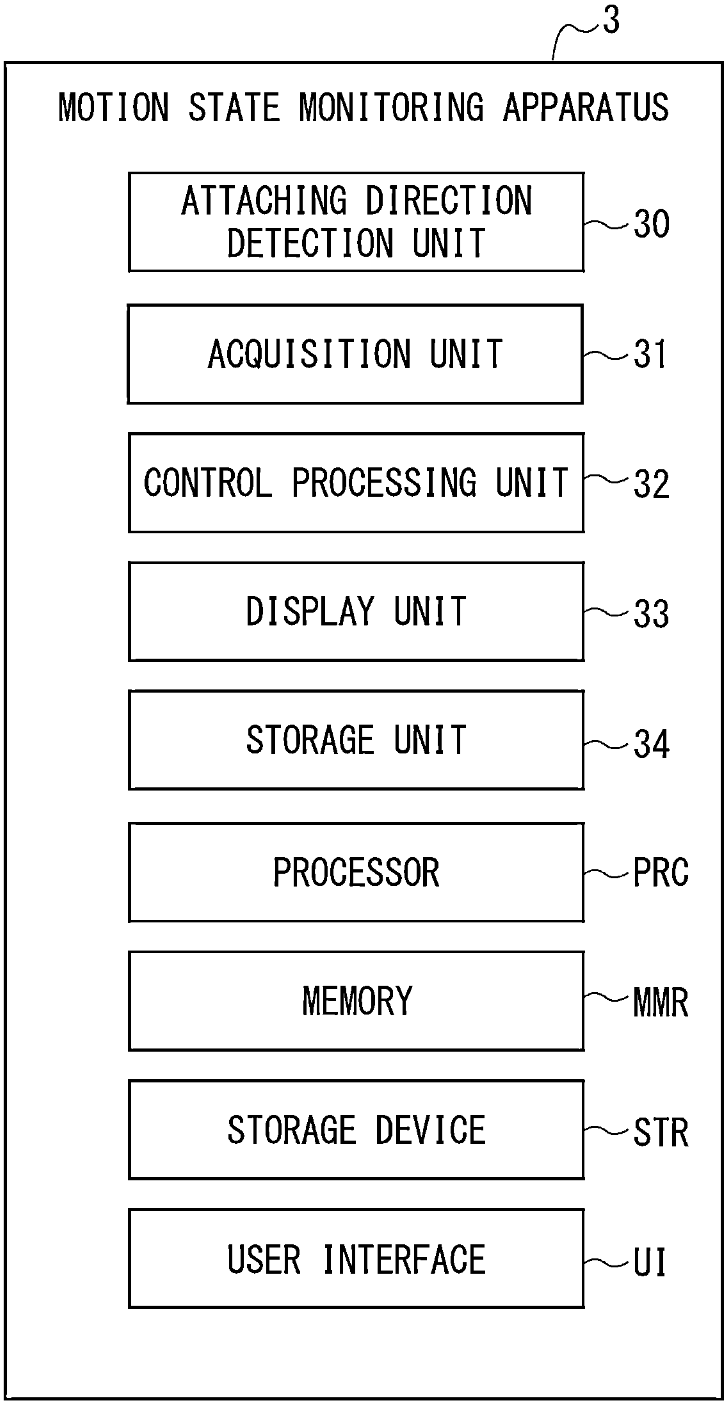
FIG. 16 is a general configurational diagram showing an example of a motion state monitoring apparatus including a computer according to an embodiment.

FIG. 16 is a general structural diagram showing an example of a motion state monitoring apparatus 3 including a computer according to the above-described embodiment. As shown in FIG. 16, the motion state monitoring apparatus 3 may further include a processor PRC, a memory MMR, a storage device STR, and a user interface UI. In the storage device STR, a process performed by each of the components of the motion state monitoring apparatus 3 are stored in the form of a computer program(s). Further, the processor PRC loads the program from the storage device STR onto the memory MMR, and executes the loaded program. In this way, the processor PRC implements the function of each of the components in the motion state monitoring apparatus 3. The user interface UI may include an input device such as a keyboard, a mouse, and a photographing apparatus, and an output device such as a display, a printer, and a speaker.

Each of the components included in the motion state monitoring apparatus 3 may be implemented by dedicated hardware. Further, some or all of the components may be implemented by, for example, a general purpose or dedicated circuit (Circuitry), a processor PRC, or a combination thereof. These components may be formed by a single chip or a plurality of chips connected to each other through a bus. Some or all of the components may be implemented by any combination of the above-described circuits and programs. Further, as the processor PRC, a CPU (Central Processing Unit), a GPU (Graphics Processing Unit), an FPGA (Field-programmable Gate Array), a quantum processor (quantum computer control chip) or the like can be used.

Further, when some or all of the components of the motion state monitoring apparatus 3 are implemented by a plurality of information processing apparatuses, circuits, or the like, the plurality of information processing apparatuses, circuits, or the like may be centralized in one place or distributed over a plurality of places. For example, the information processing apparatuses, circuits, or the like may be implemented by a client-server system, a cloud computing system, or the like in a form in which the apparatuses or the like are connected to each other through a communication network NW. Further, the function of the motion state monitoring apparatus 3 may be provided in a Saas (Software as a Service) form.

The order of executions of processes in the apparatus and method shown in the claims, the specification, and the drawings may be implemented in any order unless it is specifically indicated as “before”, “prior to”, or the like, and unless an output of the preceding process is used in the subsequent process. Even when the flow of operations in the claims, the specification, and the drawings is explained by using a term such as “Firstly”, “Then”, or the like for the sake of convenience, it does not mean that it is necessary to implement the processes in this order.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A motion state monitoring system configured to monitor a motion state at a target part of a subject's body, comprising:

a measuring instrument configured to measure the motion state; and a motion state monitoring apparatus configured to monitor the motion state, wherein the measuring instrument comprises:

a sensor configured to detect the motion state; and a holding part configured to hold the sensor, the holding part comprises a bag formed of a stretchable member, the bag includes an insertion opening extending in one direction and is configured to hold thereinside the sensor inserted through the insertion opening, and when the holding part holding thereinside the sensor is attached to the target part, the holding part is attached to the target part in such a manner that the bag stretches in the one direction, the insertion opening stretches in the one direction, and the insertion opening narrows such that the sensor is prevented from falling out of the bag.

2. The motion state monitoring system according to claim 1, wherein the bag comprises a cloth as a material, and a lid configured to cover the insertion opening.

3. The motion state monitoring system according to claim 1, wherein the measuring instrument further comprises an attaching part configured to be attached to the target part, and the holding part is attached to the target part with the attaching part stretchable in the one direction interposed therebetween.

4. The motion state monitoring system according to claim 3, wherein a hole is formed at a part corresponding to a predetermined position in the target part in each of the holding part and the attaching part, and a part of the attaching part located on a side thereof on which the subject's body is located is black.

5. The motion state monitoring system according to claim 3, wherein the holding part is attached to the attaching part by hook-and-loop fasteners.

6. The motion state monitoring system according to claim 1, wherein the holding part comprises a transparent part configured to let light emitted from a light emitting unit provided in the sensor pass therethrough.

7. The motion state monitoring system according to claim 1, wherein the motion state monitoring apparatus comprises:

an acquisition unit configured to acquire sensing information of the sensor attached to the target part;

an attaching direction detecting unit configured to detect an attaching direction of the sensor; and a control processing unit configured to output sensing-related information related to the sensing information in association with the attaching direction of the sensor.

8. The motion state monitoring system according to claim 7, wherein the attaching direction of the sensor is an attaching direction with respect to a direction determined in advance according to the target part.

9. The motion state monitoring system according to claim 7, wherein the attaching direction of the sensor is an attaching direction with respect to an axial direction of the attaching part attached to the target part.

10. The motion state monitoring system according to claim 7, wherein the control processing unit outputs, in response to detection of an event in which the attaching direction changes during measurement by the sensor, the sensing-related information obtained after the event in association with the changed attaching direction after the event.

11. The motion state monitoring system according to claim 7, wherein the control processing unit performs an arithmetic processing according to the attaching direction on the sensing information or the sensing-related information, and outputs a result of the arithmetic processing in association with the attaching direction of the sensor.

12. A motion state monitoring method for monitoring a motion state at a target part of a subject's body by using a motion state monitoring system, wherein the motion state monitoring system comprises:

a measuring instrument configured to measure the motion state; and a motion state monitoring apparatus configured to monitor the motion state, the measuring instrument comprises:

a sensor configured to detect the motion state; and a holding part configured to hold the sensor, the holding part comprises a bag formed of a stretchable member, the bag includes an insertion opening extending in one direction and is configured to hold thereinside the sensor inserted through the insertion opening, when the holding part holding thereinside the sensor is attached to the target part, the holding part is attached to the target part in such a manner that the bag stretches in the one direction, the insertion opening stretches in the one direction, and the insertion opening narrows such that the sensor is prevented from falling out of the bag, and the motion state monitoring method comprises:

acquiring sensing information of a sensor attached to the target part;

detecting an attaching direction of the sensor; and outputting sensing-related information related to the sensing information in association with the attaching direction of the sensor.

* * * * *